US008182815B2

(12) United States Patent
Sun et al.

(10) Patent No.: US 8,182,815 B2
(45) Date of Patent: May 22, 2012

(54) FIBROBLAST GROWTH FACTOR RECEPTOR-3 (FGFR-3) INHIBITORS AND METHODS OF TREATMENT

(75) Inventors: Haijun Sun, New York, NY (US); Ling Liu, Carmel, IN (US)

(73) Assignee: ImClone, LLC, New York, NY (US)

( * ) Notice: Subject to any disclaimer, the term of this patent is extended or adjusted under 35 U.S.C. 154(b) by 0 days.

(21) Appl. No.: 13/235,900

(22) Filed: Sep. 19, 2011

(65) Prior Publication Data

US 2012/0009200 A1  Jan. 12, 2012

Related U.S. Application Data

(62) Division of application No. 12/579,825, filed on Oct. 15, 2009, now Pat. No. 8,043,618.

(60) Provisional application No. 61/196,855, filed on Oct. 20, 2008.

(51) Int. Cl.
*A61K 39/395* (2006.01)
*C07K 16/28* (2006.01)
*C07K 16/00* (2006.01)

(52) U.S. Cl. ............... 424/143.1; 424/139.1; 530/387.9; 530/388.22

(58) Field of Classification Search .......................... None
See application file for complete search history.

(56) References Cited

U.S. PATENT DOCUMENTS

| 4,946,778 | A | 8/1990 | Ladner | |
|---|---|---|---|---|
| 7,960,518 | B2 * | 6/2011 | Throsby et al. | 530/388.2 |
| 8,012,474 | B2 * | 9/2011 | Fischer et al. | 424/130.1 |
| 8,043,618 | B2 * | 10/2011 | Sun et al. | 424/143.1 |
| 2005/0147612 | A1 | 7/2005 | Yayon | |
| 2007/0248605 | A1 | 10/2007 | Hestir | |

FOREIGN PATENT DOCUMENTS

| EP | 1423428 | 2/2004 |
|---|---|---|
| WO | 8809344 | 12/1988 |
| WO | 02102972 | 12/2002 |
| WO | 2005066211 | 7/2005 |

OTHER PUBLICATIONS

Gomez-Roman et al. Fibroblast Growth Factor Receptor 3 Is Overexpressed in Urinary Tract Carcinomas and Modulates the Neoplastic Cell Growth. Clinical Cancer Research. vol. 11, 459-465 (Jan. 15, 2005).*
Abath, et al., A Simple Method for the Recovery of Purified Recombinant Peptides Cleaved from Glutathione-S-Transferase-Fusion Proteins, Peptide Research 3(4):167-168 (1990).
Batley, et al., Inhibition of FGF-1 Receptor Tyrosine Kinase Activity by PO 161570, a New Protein-Tyrosine Kinase Inhibitor, Life Sci. 62:143-150 (1998).
Boerner, et al., Production of Antigen-Specific Human Monoclonal Antibodies from in Vitro-Promed Human Splenocytes, J. Immunol. 147(1):86-95 (1991).
Burdon, et al. eds., Laboratory Techniques in Biochemistry and Molecular Biology, vol. 13, pp. 1-260 (Elsevier Science Publishers, Amsterdam) in Monoclonal Antibody Technology, The Production and Characterization of Rodent and Human Hybridomas (Campbell ed., 1984).
Intentionally Omitted [Campbell, Monoclonal Antibody Technology. The Production and Charaterization of Rodent and Human Hybridomas, Elsevier Science Publishers, Amsterdam, New York (1984>>).
Chellaiah, et al., Mapping ligand Binding Domains in Chimeric Fibroblast Growth Factor Receptor Molecules, J . Biol. Chem 274(49):34785-34794 (1999).
Chothia, et al., Canonical Structures for the Hypervariable Regions of Immunoglobulins, J . Mol. Biol. 196 (4):901-917 (1987).
Cole, et al., The EBV-Hybridoma Technique and lis Application to Human Lung Cancer, Monoclonal Antibodies and Cancer Therapy, Alan R. liss Inc. pp. 77-96 (1985).
Deevi, et al., AACR Abstract No. 2329, Mechanism for the Benefits of Cetuximab in Combination with Oxaliplatin, in Oxaliplatin Sensitive and Resistant Colon Cancer Cell Lines (Oct. 21-24, 2007).
Dieckmann, et al ., Assembly of the Mitochondrial Membrane System, J. Bioi. Chem. 260:1513-1520 (1985).
Hawkins, et al., Selection of Phage Antibodies by Binding Affinity Mimicking Affinity Maturation, J. Mol. Biol., 226:889-896 (1992).
Hoogenboom, et al.. By-passing Immunisation Human Antibodies from Synthetic Repertoires of Germline Vh Gene Segments Rearranged in vitro, J. Mol. Biol. 227(2):381-388 (1992).
Huse, et al. , Generation of a large Combinatorial library of the Immunoglobulin Repertoire in Phage lambda, Science 246:1275-1281 (1989).
Kabat, et al ., Attempts to Locate Complementarity-Determining Residues in the Variable Positions of Light and Heavy Chains, Ann . NY Acad. Sci. 190:382-393 (1971).
Kabat, et al ., Sequences of Proteins of Immunological Interest, Fifth Edition, U.S. Department of Health and Human Services, No. 91-3242 (1991 ).
Kohler, et al., Continuous Cultures of Fused Cells Secreting Antibody of Predefined Specificity, Nature 256:495-497 (1975).
Low, et al., Mimicking Somatic Hypermutation: Affinity Maturation of Antibodies Displayed on Bacteriophage Using a Bacterial Mutator Strain, J. Mol. Biol. 250:359-368 (1996).
Marks, et al., By-passing Immunization Human Antibodies from V-gene libraries Displayed on Phage, J. Mol. Bioi. 222(3):581-597 (1991).
Martin, A.C.R. Accessing the Kabat Antibody Sequence Database by Computer Proteins: Structure, Function and Genetics, 25,130-133 (1996).
Martinez-Torrecuadrada. et al .* Targeting the Extracellular Domain of Fibroblast Growth Factor Receptor 3 20 with Human Single-Chain Fv Antibodies Inhibits Bladder Carcinoma Cell Line Proliferation, Clin. Cancer Res.;11 0 (17):6280-6290 (2005).

(Continued)

Primary Examiner — Elizabeth C Kemmerer
Assistant Examiner — Regina M Deberry
(74) Attorney, Agent, or Firm — Averie K. Hason

(57) ABSTRACT

The present invention relates to an isolated antibody or fragment thereof, which specifically binds to human FGFR-3 (IIIb) and FGFR-3(IIIc), or mutant forms thereof. Further embodiments include pharmaceutical compositions comprising the antibody and methods of using the antibody to treat cancer.

5 Claims, No Drawings

OTHER PUBLICATIONS

Panek, et al., In Vitro Pharmacological Characterization of PD 166285, a New Nanomolar Potent and Broadly Active Protein Tyrosine Kinase Inhibitor, J. Pharmacol. Exp. Ther. 283:1433-1444 (1997).

Qing, el. al., Antibody-based targeting of FGFR3 in bladder carcinoma and t(4;14)-positive multiple myeloma in mice, Journal of Clinical Investigation 119 (5):1216-1229 (2009).

Rauchenberger, et al., Human Combinatorial Fab Library Yielding Specific and Functional Antibodies against the Human Fibroblast Growth Factor Receptor 3, J. Biol. Chem. 278(40):38194-38205 (2003).

Sambrook, et al., Molecular Cloning: A Laboratory Manual, 2nd Edition, Chapter 1-18, Cold Spring Harbor Laboratory Press (1989).

Smith, et al., Single-Step Purification of Polypeptides Expressed in *Escherichia coli* as Fusions with Glutathione S-transferase, Gene 67(1):31-40 (1988).

Savillo, et al., Neutralizing antibodies to FGF receptor 1 and 3 inhibit tumor growth in mouse xenograft studies, Author's slides from presentation, Cordon, Ventura, CA (Mar. 2006); no abstract No. available.

Yu, et al., FGF signaling in osteosarcoma tumor cells, Author's slides from presentation at MCR, Washington, DC (Apr. 2006); no abstract No. available.

Direnzo, et al., Neutralizing antibody against FGFR3 shows antitumor effects in multiple tumor models in vivo, MCR Abstract No. 2080, Los Angeles, CA (Apr. 2007).

Sun, et al., A neutralizing monoclonal antibody specific for fibroblast growth factor receptor-3 (FGFR-3) suppresses growth of human prostate tumor cells in vitro and in vivo. Author's slides from presentation at MCR EORTC. Boston, MA (Nov. 2003); no abstract No. available.

Sun, et al., Targeting fibroblast growth factor-signaling in tumor cells using monoclonal antibodies, Author's slides from presentation at AACR-EORTC. Philadelphia, PA (Nov. 2005); no abstract No. available.

Wang, et al., Transcriptome analysis method for in vivo mechanism of action study: IMC-D11 anti-FGFR3 +/− cisplatin in bladder cancer models, AACR-EORTC Abstract ND. 200, Geneva, Switzerland (Nov. 2008).

Sun, et al., Targeting FGFR pathways using monoclonal antibodies, Author's slides from presentation at FGF Conference, Kobe, Japan (Oct. 2003); no abstract No. available.

Deevi, et al., Inhibiting FGFR3 for enhancing the cytotoxic effects of cisplatin on bladder cancer cells and possible mechanisms, AACR-EORTC Abstract No. 848, San Francisco, CA (Oct. 2007).

Trudel, et al., The inhibitory anti-FGFR3 antibody, PRO-OO1, is cytotoxic to t(4;14) multiple myeloma cells, Blood 107(10):4039-4046 (2006).

Wu, et al., Humanization of a Murine Monoclonal Antibody by Simultaneous Optimization of Framework and CDR Residues, J. Mol. Biol., 294:151-162 (1999).

Xin, et al., CHIR-258 Is Efficacious in a Newly Developed Fibroblast Growth Factor Receptor 3—Expressing Orthotopic Multiple Myeloma Model in Mice, Clin Cancer Res. 12(16):4908-4915 (2006).

Yang, et al. CDR Walking Mutagenesis for the Affinity Maturation of a Potent Human Anti-HIV-1 Antibody into the Picomolar Range, J. Mol. Biol. 254:392-403 (1995).

Dvorak, et al., Increased expression of fibroblast growth faclor receptor 3 in CD34+ BCR-ABL+ cells from patients with chronic myeloid leukemia, Leukemia 17(12):2418-2425 (2003).

Keegan, et al., Isolation of an additional member of the fibroblast growth factor receptor family. FGFR-3. Proc Natl D Acad. Sci. 88:1095-1099 (1991).

Scotet, et al., The choice between alternative IIIb and IIIc exons of the FGFR-3 gene is not strictly tissue-specific, Biochimica Et Biophysica ACTA 1264(2)238-242 (1995).

Portolano, et al., Lack of promiscuity in autoantigen-specific H and L chain combinations as revealed by Human H and L chain "roulette". The Journal of Immunology, vol. 15013:880-887 (1993).

Clackson, et al. Making antibody fragments using phage display libraries. Nature, vol. 352 (Aug. 1991).

Pascalis, et al. Grafting of "abbreviated" complementarity-determining regions containing specificity-determining residues essential for ligand contact to engineer a less immunogenic humanized monoclonal antibody. The Journal of Immunology, vol. 169:3076-3084 (2002).

Dominiques-Escrig et al. Evaluation of the therapeutic potential of the epidermal growth factor receptor tyrosine kinase inhibitor gefitinib in preclinical models of bladder cancer. Clinical Cancer Research 10:4874-4884 (Jul. 2004).

Singh et al. Oral silibinin in vivo human bladder tumor xenograft growth involving down-regulation of survivin. Clinical Cancer Res 14(1) (Jan. 2008).

Hsi et al. CS1, a potential new therapeutic antibody target for the treatment of multiple myeloma. Clin. Cancer Res 14:2775-2784 (May 2008).

* cited by examiner

FIBROBLAST GROWTH FACTOR RECEPTOR-3 (FGFR-3) INHIBITORS AND METHODS OF TREATMENT

This application is a divisional of U.S. application Ser. No. 12/579,825 filed 15 Oct. 2009, which claims priority to U.S. Provisional application No. 61/196,855 filed 20 Oct. 2008.

This invention is in immunology and cancer treatment. More specifically, the present invention is directed to a human antibody that binds to human fibroblast growth factor receptor 3 (FGFR-3) (SEQ ID NO 11). FGFR is also known as CD333, ACH, CEK2, HSFGFR-3EX and JTK4.

FGFR-3 has been shown to be involved in the development of cancer, including multiple myeloma, bladder and urothelial cell carcinoma. FGF ligand-receptor binding induces receptor dimerization and autophosphorylation, leading to down-stream activation of effector molecules. FGFR-3 signaling is capable of regulating a broad range of cellular activities such as proliferation, differentiation, migration, survival/apoptosis, cytoskeleton and cytokine regulation, and endocytosis/exocytosis. Hyper-activation of FGFR-3 signaling has been recognized as an important event that affords tumor cells with a growth or survival advantage and thus contributes to tumor malignancy.

Full length FGFR-3 has two splice forms called FGFR-3(IIIb) and FGFR-3(IIIc) that result from alternative exons encoding the third IgG-like domain of FGFR-3. FGFR-3 also has well documented mutant forms due to errors in DNA replication or translation. Given the active role of the FGFR-3 signaling pathway in a wide range of diseases including cancer, there is a need for a mechanism by which to regulate this pathway.

Anti-FGFR-3 antibodies that block ligand binding have been disclosed. (Rauchenberger, R. et al., J. Biol. Chem. 2003 Oct. 3; 278(40):38194-205.) Anti-FGFR-3 antibodies that bind to both wild type and mutant forms of FGFR-3 have been disclosed. (Martinez-Torrecuadrada, J., et al., Clin. Cancer Res. 2005 Sep. 1; 11(17):6280-90; Trudel S., et al., Blood 2006 May 15; 107(10):4039-46.) Anti-FGFR-3 antibodies that inhibit ligand mediated activation of FGFR-3 signaling, and inhibit FGFR-3-mediated tumor growth have been disclosed. (Trudel S., et al., Blood 2006 May 15; 107(10):4039-46.) Anti-FGFR-3 antibodies that enhance the anti-tumor effects of cisplatin when given as combination therapy have been disclosed. (Deevi, D. et al., AACR 2007 Oct. 21-24; Wang, W., et al., EORTC 2008 Oct. 22-26.)

However, there is a need in the art for an antibody antagonist that is capable of one or more of the following: is highly specific to both splice forms of FGFR-3, (FGFR-3(IIIb) and FGFR-3(IIIc)), that internalizes FGFR-3 and that preferably also induces degradation of FGFR-3(IIIb) and FGFR-3(IIIc) or mutant forms thereof, and that enhances therapeutic efficacy and reverses chemo-resistance when used in combination with a chemo cytotoxic agent. Additionally, the antibody is preferably also active to mutant forms of FGFR-3, blocks FGF ligands from binding to FGFR-3, inhibits ligand-induced FGFR-3 signaling pathways, inhibits FGFR-3-mediated cellular activities, or inhibits tumor growth in vitro and in vivo.

The antibody of the invention has solved these needs. The antibody is highly specific to both splice forms of FGFR-3, (FGFR-3(IIIb) and FGFR-3(IIIc)), internalizes FGFR-3 and preferably also induces receptor degradation upon binding to FGFR-3 receptors or receptor mutants in cells thereof, enhances therapeutic efficacy and reverses chemo-resistance when used in combination with a chemo cytotoxic agent, as well as is active to mutant forms of FGFR-3, blocks FGF ligands from binding to FGFR-3, inhibits ligand-induced FGFR-3 signaling pathways, inhibits FGFR-3-mediated cellular activities, and inhibits tumor growth in vitro and in vivo.

The invention relates to an isolated antibody that specifically binds to human FGFR-3(IIIb) and FGFR-3(IIIc).

Preferably, the antibody is a human antibody having a $K_D$ of about $1 \times 10^{-8}$ M or less at room temperature (20-25° C.).

Preferably, the antibody specifically binds to human FGFR-3 domain 2 (SEQ ID NO 12).

Preferably, the antibody of the invention that specifically binds to human FGFR-3(IIIb) and FGFR-3(IIIc), comprising a CDRH1 having the sequence GYMFTSYGIS (SEQ ID NO 1), a CDRH2 having the sequence WVSTYNGDTNYAQKFQG (SEQ ID NO 2), a CDRH3 having the sequence VLGYYDSIDGYYYGMDV (SEQ ID NO 3), a CDRL1 having the sequence GGNNIGDKSVH (SEQ ID NO 4), a CDRL2 having the sequence LDTERPS (SEQ ID NO 5), and a CDRL3 having the sequence QVWDSGSDHVV (SEQ ID NO 6).

Preferably, the antibody may comprise a variable heavy amino acid sequence of EVQLVQSGAEVKKPGASVKVSCKASGYMFTSYGISWVRQAPGQGLEWMGWVS TYNGDTNYAQKFQGRVTVTTDTSTSTAYMELRSLRSEDTAVYYCARVLGYYDSI DGYYYGMDVWGQGTTVTVSS (SEQ ID NO 7) and a variable light amino acid sequence of QSVLTQPPSLSVAPGKTATFTCGGNNIGDKSVHWYRQKPGQAPVLVMYLDTERP SGIPERMSGSNFGNTATLTITRVEAGDEADYYCQVWDSGSDHVVFGGGTKLTVL G (SEQ ID NO 8).

Preferably, the antibody may comprise a variable heavy amino acid sequence of EVQLVQSGAEVKKPGASVKVSCKASGYMFTSYGISWVRQAPGQGLEWMGWVS TYNGDTNYAQKFQGRVTVTTDTSTSTAYMELRSLRSEDTAVYYCARVLGYYDSI DGYYYGMDVWGQGTTVTVSS (SEQ ID NO 7) or a variable light amino acid sequence of QSVLTQPPSLSVAPGKTATFTCGGNNIGDKSVHWYRQKPGQAPVLVMYLDTERP SGIPERMSGSNFGNTATLTITRVEAGDEADYYCQVWDSGSDHVVFGGGTKLTVL G (SEQ ID NO 8).

The antibody heavy constant region may be from human IgG1, or an FGFR-3-binding fragment of the antibody. Preferably, the antibody comprises a heavy chain of SEQ ID NO: 9 and a light chain of SEQ ID NO: 10. Preferably, the antibody comprises a heavy chain of SEQ ID NO: 9 and a light chain of SEQ ID NO: 10, or an FGFR-3-binding fragment of the antibody.

The antibody may also comprise two heavy chains of SEQ ID NO: 9 and two light chains of SEQ ID NO: 10. The antibody may also comprise two heavy chains of SEQ ID NO: 9 and two light chains of SEQ ID NO: 10. Preferably, the antibody comprises two heavy chains of SEQ ID NO: 9 and two light chains of SEQ ID NO: 10, or an FGFR-3-binding fragment of the antibody.

The antibody may comprise a neutralizing human FGFR-3 binding fragment.

In a preferred aspect, the invention is directed to an isolated antibody or a fragment thereof, wherein said antibody competes for binding to the extracellular domain of FGFR-3 in a competition ELISA assay with a competing antibody, wherein said competing antibody binds FGFR-3 with a $K_D$ of about $1 \times 10^{-8}$ M or less at room temperature (20-25° C.).

The invention further relates to an antibody that binds to mutant forms of FGFR-3.

The present invention relates to a pharmaceutical composition comprising the antibody or fragment, and a pharmaceutically acceptable carrier, diluent or excipient.

The present invention also relates to a product containing an antibody or fragment and an additional anti-cancer agent for treatment in combination for simultaneous, separate or sequential use in therapy.

In another aspect of the invention, the antibody or fragment is for use as a medicament. In another aspect of the invention, the antibody or fragment is for use in the treatment of cancer. In another aspect of the invention, the antibody or fragment is used as a medicament where the cancer is bladder or multiple myeloma.

In another aspect of the invention, the antibody or fragment is used in the treatment of cancer together with another agent. The antibody or fragment of the invention may be administered simultaneously, separately, or sequentially with an effective amount of another agent to the patient. The invention may comprise a pharmaceutical composition comprising a compound together with a pharmaceutically acceptable carrier and optionally other therapeutic ingredients.

The invention also relates to a method of treating cancer in a patient comprising administering to the patient an effective amount of the antibody of the invention. The cancer may be bladder or multiple myeloma. In another aspect, the invention includes a method of treating cancer in a patient comprising administering simultaneously, separately, or sequentially an effective amount of the antibody of the present invention and another agent to the patient. The other agent may be cisplatin.

Accordingly, the antibody of the invention binds to naturally occurring and mutant forms of FGFR-3 and induce degradation of FGFR-3, are capable of inhibiting tumors by acting upon the tumor cells as well as stromal components, have broad therapeutic value in treating cancer.

The term "antibody" includes immunoglobulin molecules comprising four polypeptide chains, two identical heavy (H) chains and two identical light chains (L), interconnected by a disulfide bond. Individual chains can fold into domains having similar sizes (110-125 amino acids) and structures, but different functions.

An "isolated antibody" is an antibody that (1) has been partially, substantially, or fully purified from a mixture of components; (2) has been identified and separated and/or recovered from a component of its natural environment; (3) is monoclonal; (4) is free of other proteins from the same species; (5) is expressed by a cell from a different species; or (6) does not occur in nature. Contaminant components of its natural environment are materials which would interfere with diagnostic or therapeutic uses for the antibody, and may include enzymes, hormones, and other proteinaceous or non-proteinaceous solutes. Examples of isolated antibodies include an antibody that has been affinity purified, an antibody that has been made by a hybridoma or other cell line in vitro, or a human antibody derived from a transgenic mouse.

The term "monoclonal antibody," as used herein, refers to an antibody obtained from a population of substantially homogeneous antibodies, e.g., the individual antibodies comprising the population are substantially identical except for possible naturally occurring mutations or minor post-translational variations that may be present. Monoclonal antibodies are highly specific, being directed against a single antigenic site (also known as determinant or epitope). Furthermore, in contrast to conventional (polyclonal) antibody preparations which typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

The term "human antibody," as used herein, includes antibodies having variable and constant regions corresponding to human germline immunoglobulin sequences as described in Kabat et al., Chothia et al., and Martin, supra. The human antibody of the invention may include amino acid residues not encoded by human germline immunoglobulin sequences (e.g., mutations introduced by random or site-specific mutagenesis in vitro or by somatic mutation in vivo), for example in the complementarity-determining regions (CDRs). The human antibody can have at least one position replaced with an amino acid residue, e.g., an activity enhancing amino acid residue which is not encoded by the human germline immunoglobulin sequence. However, the term "human antibody," as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal that is transgenic for human immunoglobulin genes, or antibodies prepared, expressed, created or isolated by any other means that involves splicing of human immunoglobulin gene sequences to other DNA sequences. Such recombinant human antibodies have variable and constant regions derived from human germline immunoglobulin sequences.

The light chain can comprise one variable domain (abbreviated herein as VL) and/or one constant domain (abbreviated herein as CL). The light chains of antibodies are either kappa (κ) light chains or lambda (λ) light chains. The expression on VL, as used herein, is intended to include both the variable regions from kappa-type light chains (Vκ) and from lambda-type light chains (Vλ). The heavy chain can also comprise one variable domain (abbreviated herein as VH) and/or, depending on the class or isotype of antibody, three or four constant domains (CH1, CH2, CH3, and CH4). In humans, the isotypes are IgA, IgD, IgE, IgG, and IgM, with IgA and IgG further subdivided into subclasses or subtypes ($IgA_{1-2}$ and $IgG_{1-4}$).

The present invention includes antibodies of any of the aforementioned classes or subclasses. Human IgG is the preferred isotype for the antibody of the present invention. Three regions, called hypervariable or CDRs, are found in each of VL and VH, which are supported by less variable regions called framework regions (abbreviated herein as FR).

Amino acids are assigned to a particular CDR region or domain in accordance with Kabat convention (Kabat, et al., Ann. NY Acad. Sci. 190:382-93 (1971); Kabat, et al., Sequences of Proteins of Immunological Interest, Fifth Edition, U.S. Department of Health and Human Services, NIH Publication No. 91-3242 (1991)) or Chothia convention (C. Chothia and A. M. Lesk, J. Mol. Biol. 196 (4): 901-917 (1987)) or by Martin, (Martin, A. C. R. Accessing the Kabat Antibody Sequence Database by Computer PROTEINS: Structure, Function and Genetics, 25 (1996), 130-133.)

Each VH and VL is composed of three CDRs and four FRs, arranged from amino-terminus to carboxy-terminus in the following order: FR1-CDR1-FR2-CDR2-FR3-CDR3-FR4. The portion of an antibody consisting of VL and VH domains is designated Fv (Fragment variable) and constitutes the antigen-binding site. Single chain Fv (scFv) is an antibody fragment containing a VL domain and a VH domain on one polypeptide chain, wherein the N terminus of one domain and the C terminus of the other domain are joined by a flexible linker (see, e.g., U.S. Pat. No. 4,946,778 (Ladner et al.), WO 88/09344 (Huston et al.)).

Fragments have binding characteristics that are the same as, or are comparable to, those of the whole antibody. Suitable fragments of the antibody include any fragment that comprises a sufficient portion of the hypervariable (i.e. complementarity determining) region to bind specifically, and with sufficient affinity to inhibit growth of cells. Such fragments may, for example, contain one or both Fab fragments or the F(ab')2 fragment. Preferably the antibody fragments contain all six complementarity determining regions of the whole antibody, although functional fragments containing fewer than all of such regions, such as three, four or five CDRs, are also included. Preferred fragments are single chain antibodies, or Fv fragments. More preferred fragments are bivalent. Single chain antibodies are polypeptides that comprise at least the variable region of the heavy chain of the antibody and the variable region of the light chain, with or without an interconnecting linker. Thus, Fv fragments comprise the entire antibody combining site. These chains may be produced in bacteria or in eukaryotic cells.

Fab (Fragment, antigen binding) refers to the fragments of the antibody consisting of VL CL VH CH1 domains. Those generated following papain digestion simply are referred to as Fab and do not retain the heavy chain hinge region. Following pepsin digestion, various Fabs retaining the heavy chain hinge are generated. Those fragments with the interchain disulfide bonds intact are referred to as F(ab')2, while a single Fab' results when the disulfide bonds are not retained. F(ab')2 fragments have higher avidity for antigen that the monovalent Fab fragments.

Fc (Fragment crystallization) is the designation for the portion or fragment of an antibody that comprises paired heavy chain constant domains. In an IgG antibody, for example, the Fc comprises CH2 and CH3 domains. The Fc of an IgA or an IgM antibody further comprises a CH4 domain. The Fc is associated with Fc receptor binding, activation of complement-mediated cytotoxicity and antibody-dependent cellular-cytotoxicity (ADCC). For antibodies such as IgA and IgM, which are complexes of multiple IgG like proteins, complex formation requires Fc constant domains.

The hinge region separates the Fab and Fc portions of the antibody, providing for mobility of Fabs relative to each other and relative to Fc, as well as including multiple disulfide bonds for covalent linkage of the two heavy chains.

Thus, an antibody of the invention includes, but is not limited to, naturally occurring antibodies, human antibodies, recombinant human antibodies, monoclonal antibodies, digestion fragments, bivalent fragments such as (Fab')2, monovalent fragments such as Fab, single chain antibodies, single chain Fv (scFv), single domain antibodies, multivalent single chain antibodies, diabodies, triabodies, and the like that bind specifically with antigens.

An antibody of the present invention is specific for FGFR-3. Antibody specificity refers to selective recognition of the antibody for a particular epitope of an antigen. The antibody may exhibit both species and molecule selectivity, or may be selective with respect to molecule only and bind to FGFR-3 of more than one species. The antibody of the invention may bind to human, murine, rat, dog and/or rabbit FGFR-3. Preferably, the antibody binds to human FGFR-3. Antibody formats have been developed that retain binding specificity but that also have other characteristics.

An antibody of the present invention, for example, can be monospecific, bispecific or multispecific. Bispecific antibodies (BsAbs) are antibodies that have two different antigen-binding specificities or sites. Multispecific antibodies have more than two different antigen-binding specificities or sites. Where an antibody has more than one specificity, the recognized epitopes can be associated with a single antigen or with more than one antigen.

Specificity of the FGFR-3 antibodies can be determined based on affinity and/or avidity. Affinity, represented by the equilibrium constant for the dissociation of an antigen with an antibody ($K_D$), measures the binding strength between an antigenic determinant and an antibody-binding site. Avidity is the measure of the strength of binding between an antibody with its antigen. Avidity is related to both the affinity between an epitope with its antigen binding site on the antibody, and the valence of the antibody, which refers to the number of antigen binding sites of a particular epitope. Antibodies typically bind with a dissociation constant ($K_D$) of about $10^{-5}$ to about $10^{-11}$ mol/liters (e.g., $K_D < 100$ M). Any $K_D$ less than about $10^{-4}$ mol/liter is generally considered to indicate non-specific binding—the lesser the value of the $K_D$, the stronger the binding strength between an antigenic determinant and the antibody binding site.

In certain aspects, the antibody of the invention binds to FGFR-3 with a $K_D$ of preferably about $1\times10^{-8}$ M or less, more preferably about $1\times10^{-9}$ M or less, more preferably about $1\times10^{-10}$ M or less, and most preferably about $1\times10^{-11}$ M or less. See Table 1 below.

TABLE 1

Binding affinities of Antibody 1 to human and murine FGFR-3 splice variants.

| | $K_D$ (M) |
|---|---|
| Human FGFR-3(IIIb) | $7.2 \times 10^{-10}$ |
| Human FGFR-3(IIIc) | $1.4 \times 10^{-10}$ |
| Murine FGFR-3(IIIb) | N.D. |
| Murine FGFR-3(IIIc) | $2.2 \times 10^{-10}$ |

In certain aspects, the antibody of the present invention preferably has a $K_D$ of about $5.0\times10^{-10}$ M to about $1.5\times10^{-11}$ M, about $1.0\times10^{-10}$ M to about $1.0\times10^{-11}$ M or about $1.5\times10^{-11}$ M to about $7.5\times10^{-10}$ M.

As used herein, the terms "blocks binding" and "inhibits binding," used interchangeably, refer to blocking/inhibition of binding of a cytokine to its receptor, resulting in complete or partial inhibition or reduction of a biological function of the cytokine/receptor signal pathway. Blocking/inhibition of binding of FGF to FGFR-3 is assessed by measuring the complete or partial inhibition or reduction of one or more in vitro or in vivo indicators of FGF activity such as, receptor binding, an inhibitory effect on cell growth, chemotaxis, apoptosis, intracellular protein phosphorylation, or signal transduction. The ability to block the binding FGF to FGFR-3 may be measured by ELISA as described herein. The antibody of the invention is an antagonist that blocks the FGFR-3 receptor in ligand-induced activation in live cells. Binding assays can be carried out using a variety of methods known in the art, including, but not limited to, ELISA. As used herein, "competes for binding" refers to the situation in which an antibody reduces binding or signaling by at least about 20%, 30%, 50%, 70% or 90% as measured by a technique available in the art, e.g., competition ELISA or $K_D$ measurement with BIAcore, but is not intended to completely eliminate binding.

The heavy chain amino acid sequence is described in SEQ ID NO. 9. The light chain amino acid sequence is described in SEQ ID NO. 10. In another aspect, the antibody of the invention has one, two, three, four, five, or all six complementarity-determining regions of any one of the CDRs of Antibody 1.

The antibody of the present invention also includes those for which binding characteristics have been improved by direct mutation, methods of affinity maturation, phage display, or chain shuffling. Affinity and specificity can be modified or improved by mutating CDR and/or framework residues and screening for antigen binding sites having the desired characteristics (see, e.g., Yang et al., J. Mol. Biol. 254:392-403 (1995)). One way is to randomize individual residues or combinations of residues so that in a population of otherwise identical antigen binding sites, subsets from two to twenty amino acids are found at particular positions. Alternatively, mutations can be induced over a range of residues by error using PCR methods (see, e.g., Hawkins et al., J. Mol. Biol., (1992) 226:889 96). In another example, phage display vectors containing heavy and light chain variable region genes can be propagated in mutator strains of E. coli (see, e.g., Low et al., J. Mol. Biol. 250:359 68 (1996)).

An in vitro selection process may then be suitably used to screen these additional variable region amino acid sequences for Fab fragments having the claimed cross reactivity and in vitro. In this way further Fab fragments are identified that are suitable for preparing a humanized antibody in accordance with the present invention. Preferably the amino acid substitution within the frameworks is restricted to one, two or three positions within one or each of the framework sequences disclosed herein. Preferably amino acid substitution within the CDRs is restricted to one to three positions within one or each CDR, more preferably substitution at one or two amino acid positions within one or each CDR is performed. Further preferred, amino acid substitution is performed at one or two amino acid positions in the CDRs of the heavy chain variable region. A suitable methodology for combining CDR and framework substitutions to prepare alternative antibodies according to the present invention, using an antibody described herein as a parent antibody, is provided in Wu et al., J. Mol. Biol., 294:151-162.

The antibody of the invention may be produced by methods known in the art. These methods include immunological methods described by Kohleer and Milstein in Nature 256: 495-497 (1975) and Campbell in "Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1985); as well as by the recombinant DNA method described by Huse et al. in Science 246:1275-1281 (1989).

Human antibodies can also be produced using various techniques known in the art, including phage display libraries (Hoogenboom and Winter, J. Mol. Biol. 227:381 (1991); Marks et al., J. Mol. Biol. 222:581 (1991)). The techniques of Cole et al. and Boemer et al. are also available for the preparation of human monoclonal antibodies (Cole et al., Monoclonal Antibodies and Cancer Therapy, Alan R. Liss, p. 77 (1985) and Boemer et al., J. Immunol. 147(1):86-95 (1991)). The antibody of the invention secreted by subclones may be isolated or purified from culture medium or ascites fluid by conventional immunoglobulin purification procedures such as, for example protein A-Sepharose, hydrolyapatite chromatography, gel electrophoresis, dialysis, or affinity chromatography.

The polynucleic acid that encodes for the antibody of the invention is obtained by standard molecular biology techniques.

The invention also includes host cells for transformation of vectors and expression of antibodies. Preferred host cells include mammalian cells, such as NSO (non-secreting (O)) mouse myeloma cells, 293 and CHO cells, and other cell lines of lymphoid origin such as lymphoma, myeloma, or hybridoma cells. Other eukaryotic hosts, such as yeast, can be used.

Vectors for expressing proteins in bacteria, especially E. coli, are known. Such vectors include the PATH vectors described by Dieckmann and Tzagoloff in J. Biol. Chem. 260:1513-1520 (1985). These vectors contain DNA sequences that encode anthranilate synthetase (TrpE) followed by a polylinker at the carboxy terminus Other expression vector systems are based on beta-galactosidase (pEX); lambda PL; maltose binding protein (pMAL); and glutathione S-transferase (pGST). See Gene 67:31 (1988) and Peptide Research 3:167 (1990).

Vectors useful in yeast are available. A suitable example is the lambda ZAP plasmid. Suitable vectors for expression in mammalian cells are also known. Such vectors include well-known derivatives of SV-40, adenovirus, retrovirus-derived DNA sequences and shuttle vectors derived from combination of functional mammalian vectors, such as those described above, and functional plasmids and phage DNA.

The vectors useful in the present invention contain at least one control element that is linked to the DNA sequence or fragment to be expressed. The control element is inserted in the vector in order to control and regulate the expression of the cloned DNA sequence.

Following expression in a host cell maintained in a suitable medium, the polypeptide to be expressed may be recovered from the medium and purified by methods known in the art. If the polypeptide or peptide is not secreted into the culture medium, the host cells are lysed prior to isolation and purification.

This invention further provides a pharmaceutical composition comprising the antibody, polynucleic acid, vector or host cell of this invention together with a pharmaceutically acceptable carrier, excipient or diluent. The pharmaceutical composition may comprise an additional therapeutic agent. The additional agent may be a chemotherapeutic agent, for example, cisplatin.

Carrier as used herein includes pharmaceutically acceptable carriers, excipients, or stabilizers which are nontoxic to the cell or mammal being exposed thereto at the dosages and concentrations employed. Often the physiologically acceptable carrier is an aqueous pH buffered solution. In another aspect of the invention, anti-FGFR-3 antibodies or antibody fragments can be chemically or biosynthetically linked to anti-tumor agents or detectable signal-producing agents, particularly when the antibody is internalized. An antibody to FGFR-3 can inhibit activation of the receptor (phosphorylated FGFR-3) as well as activation of the down-stream signaling molecules, including phosphor-MAPK and phosphor-AKT in several cancer cells, such as bladder cancer cells, which results in inhibition of their proliferative ability.

The antibody of the present invention can bind to naturally occurring FGFR-3 or its splice forms or mutants thereof "Splice forms" of FGFR-3 means the forms of the exons encoding the third IgG-like domain of FGFR-3 called FGFR-3(IIIb) and FGFR-3(IIIc). Mutant FGFR-3 includes those forms of the receptor altered by DNA replication or errors in translation. The mutations can be gain-of-function mutations that heighten the activity of the mutant receptors through mechanisms such as constitutive activation, prolonged half-life and increased ligand sensitivity.

The antibody of the present invention can bind to wild-type FGFR-3 domain 2 (SEQ ID NO 12). An arginine residue at position 173 of the human and mouse FGFR-3 sequences is not shared by the other family members, suggesting that this residue is likely responsible for the FGFR-3 specificity exhibited by Antibody 1.

The antibody of the present invention induces degradation of FGFR-3. Degrade means disintegrate the receptor so that it can no longer perform its signaling function.

The antibody of the present invention can neutralize activation of FGFR-3. Neutralizing a receptor means inactivating the intrinsic kinase activity of the receptor to transduce a signal. Neutralization for example may occur by an antibody blocking access of certain epitopes to a ligand, or by changing conformation of FGFR-3 in a certain manner so that the ligand, particularly FGF, cannot activate the receptor even though it can bind to the receptor. Down regulation may occur when cells that express FGFR-3 decrease the number of FGFR-3 receptors on their surface, for example, by inducing internalization or degradation of the receptor, or inhibiting the expression of FGFR-3. Hence, neutralizing has various effects, including inhibition, diminution, inactivation and/or disruption of growth (proliferation and differentiation), angiogenesis (blood vessel recruitment, invasion, and metastasis), and cell motility and metastasis (cell adhesion and invasiveness).

One measure of FGFR-3 neutralization is inhibition of the tyrosine kinase activity of the receptor. Tyrosine kinase inhibition can be determined using well-known methods; for example, by measuring the autophosphorylation level of recombinant kinase receptor, and/or phosphorylation of natural or synthetic substrates. Thus, phosphorylation assays are useful in determining neutralizing antibodies in the context of the present invention. Phosphorylation can be detected, for example, using an antibody specific for phosphotyrosine in an ELISA assay or on a western blot. Some assays for tyrosine kinase activity are described in Panek et al., J. Pharmacol. Exp. Ther. 283:1433-44 (1997) and Batley et al., Life Sci. 62:143-50 (1998).

In addition, the antibody of the invention can inhibit signaling by the tumor cells themselves since many tumor cells have FGFR-3 on their cell surface. The antibody of the invention can be used to treat a mammal in need thereof "Treating" a disease includes inhibiting the disease, arresting or retarding its development; relieving the disease, or causing regression of the symptoms of the disease.

The antibody and compositions of the invention can be used to treat cancer. The cancer may be refractory or first line. Cancers include, but are not limited to, brain, lung, squamous cell, bladder, gastric, pancreatic, breast, head, neck, renal, kidney, ovarian, prostate, colon, colorectal, esophageal, gynecological (ovarian, endometrial), prostate, stomach, or thyroid cancer, leukemia, and lymphoma. Additionally, cancers that may be treated by the antibody and compositions of the invention include multiple myeloma, colorectal carcinoma, Ewing's sarcoma, choriocarcinoma.

Administration is achieved by any suitable route of administration, including injection, infusion, orally, parenterally, subcutaneously, intramuscularly or intravenously.

The method of treatment described herein may be carried out with the antibody being administered with another treatment, such as anti-neoplastic agents. The anti-neoplastic treatment may include small organic molecules. Examples of such small organic molecules include cytotoxic and/or chemotherapeutic agents such as taxol, doxorubicin, actinomycin-D, cisplatin, methotrexate, irinotecan (CPT-11), gemcitabine, oxyplatin, fluorouracil (5-FU), leucourin (LU), cisplatin, paclitaxel, docetaxel, vinblastine, epothilone, cisplatin/carboplatin and Pegylated adriamycin. A preferred treatment of the invention is administration of the antibody with cisplatin.

The anti-neoplastic agent can also be radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity of the tumor being treated and the route of administration of the agent. The present invention is not limited to any particular dose.

The administration of the FGFR-3 antibodies with other antibodies and/or treatments may occur simultaneously, or separately, via the same or different route, at the same or different times. Further, the antibody may be conjugated with one or more of the other agents for administration.

The methods of treatment described herein can be used to treat any suitable mammal, including primates, such as monkeys and humans, horses, cows, cats, dogs, rabbits, and rodents such as rats and mice. Preferably, the mammal to be treated is human.

EXAMPLES

The following examples are offered for illustrative purposes only, and are not intended to limit the scope of the present invention in any way. The examples do not include detailed descriptions of conventional methods, such as those employed in the construction of vectors and plasmids, the insertion of genes encoding polypeptides into such vectors and plasmids, or the introduction of plasmids into host cells. Such methods are well known to those of ordinary skill in the art and are described in numerous publications including Sambrook, J., Fritsch, E. F. and Maniatis, T. (1989) Molecular Cloning: A Laboratory Manual, 2nd Edition, Cold Spring Harbor Laboratory Press.

Example 1

Generation of FGFR-3 Specific Antibody Antagonist

Recombinant human FGFR-Fc, recombinant human FGFs, custom-synthesized primers, restriction enzymes and DNA polymerases may be obtained from vendors or prepared by known methods.

Pan a naïve human Fab bacteriophage library against the human FGFR-3 extracellular domain with tubes coated with 10 µg FGFR-3(IIIc) extracellular domain (ECD)-Fc recombinant proteins according to published panning protocols. Elute the retained phages from the panning process and infect bacterial host cells with the retained phages. Collect phages produced by the host cells. Repeat the above procedures one more time. Transfer single colonies of infected host cells into 96-well plates containing 100 µl well of 2×YTAG, and grow phage in presence of 10 µl M13KO7 helper phage (5×10$^{10}$ pfu/ml). Incubate plates at 37° C. for 30 min without shaking followed by 30 min with shaking (100 rpm). Prepare cell pellets by centrifugation at 2,500 rpm for 10 min, resuspended in 200 µl of 2×YTAK, and incubate at 30° C. with shaking (100 rpm) for overnight. Centrifuge the plates at 2,500 rpm for 10 min. Transfer supernatants in fresh plates and mix with 6× blocking buffer (18% milk/PBS) for 1 hr. Screen phage clones using the ELISA binding and blocking assays as described below. Select phage clones that bind to FGFR-3(IIIb) or FGFR-3(IIIc), then from this pool, select those that block the receptors from binding to FGF-1 ligand. Determine DNA sequences of the clones that both bind and block the receptor according to standard sequence techniques. Each unique DNA sequence is kept and the corresponding phage clone is designated as a FGFR-3 blocker phage candidates. Prepare soluble Fabs from these phage candidates. Repeat ELISA binding and blocking assays using purified Fabs to confirm blocking activity. Engineer the confirmed Fab blockers into full size antibodies by cloning the CDRs (SEQ ID NO. 1-6) into a human IgG1 framework according to published techniques. Use ELISA binding assay to determine the binding of Antibody 1 to FGFR-1 (IIIb), FGFR-1 (IIIc), FGFR-2 (IIIb), FGFR-2 (IIIc), and FGFR-4 extracellular domain recombinant soluble proteins. Select antibodies that show high affinity binding to both b and c splice forms of FGFR-3, but low affinity binding to other FGFR receptors.

Example 2

Antibody 1

Antibody 1 may be biosynthesized in a suitable mammalian expression system using well-known methods and it can be purified by well-known methods.

The amino acid sequences for Antibody 1 are given below.

|  | Heavy Chain | Light Chain |
|---|---|---|
| CDR1 | GYMFTSYGIS (SEQ ID NO 1) | GGNNIGDKSVH (SEQ ID NO 4) |
| CDR2 | WVSTYNGDTNYAQKFQG (SEQ ID NO 2) | LDTERPS (SEQ ID NO 5) |
| CDR3 | VLGYYDSIDGYYYGMDV (SEQ ID NO 3) | QVWDSGSDHVV (SEQ ID NO 6) |
| V | EVQLVQSGAEVKKPGASVKV SCKASGYMFTSYGISWVRQA PGQGLEWMGWVSTYNGDTNY AQKFQGRVTVTTDTSTSTAY MELRSLRSEDTAVYYCARVL GYYDSIDGYYYGMDVWGQGT TVTVSS (SEQ ID NO 7) | QSVLTQPPSLSVAPGKTATFT CGGNNIGDKSVHWYRQKPGQA PVLVMYLDTERPSGIPERMSG SNFGNTATLTITRVEAGDEAD YYCQVWDSGSDHVVFGGGTKL TVLG (SEQ ID NO 8) |
| Full chain | SEQ ID NO: 9 | SEQ ID NO: 10 |

Assays

ELISA Binding Assay

Coat Recombinant FGFRS at a concentration of 1 μml in PBS on 96-well plates at room temperature for 2 hrs. Wash the plates 3 times with 0.2% Tween20/PBS, and block with 5% milk/PBS for 2 hrs before use. Add phages, Fabs or antibodies to the plate and serially dilute in 0.2% Tween20/PBS. Incubate the plate at room temperature for 2 more hrs. Detect the captured molecules using an appropriate commercial secondary antibody and detect according to suppliers' instructions.

ELISA Blocking Assay

Coat recombinant FGFs on Immulon® 2B microtiter plates (ThermoLab Systems, Franklin, Mass.) at concentrations of 0.5-2 μg/ml for 2 hrs at room temperature. Wash the plates with 0.2% Tween20/PBS, and block with 5% milk/PBS for 2 hrs before use. Serially dilute phages, Fabs, or antibodies with 5 μg/ml heparin, 5% milk, PBS. Add FGFR-3(IIIb) or (IIIc) ECD (extracellular domain) Fc tagged soluble recombinant proteins to a final concentration of 1 μg/ml. Incubate the mixture at room temperature for 1 hr before transferring to the FGF-1 coated plates, and incubate at room temperature for an additional 2 hrs. Wash plates 3 times with 0.2% Tween20/PBS. Detect the bound receptors using an anti-human Fc monoclonal antibody coupled with horse radish peroxidase (HRP) solution prepared according to supplier's instructions. Blocking activities lead to decreased signals.

Binding Affinity of Antibody 1 to Human and Mouse FGFR-3(IIIb) and FGFR-3(IIIc)

Determine the binding kinetics of the antibody to FGFR-3(IIIb) and (IIIc) using a BiaCore® 3000 biosensor (BiaCore, Inc., Piscataway, N.J.) at room temperature following the standard protocols suggested by the manufacturer. The summary of results set forth in Table 1 indicates that the antibody binds to both b and c-splice forms of human FGFR-3 as well as cross-reacting fully with mouse FGFR-3(IIIc) receptor with affinities less than $10^{-9}$ M.

Specificity of Antibody 1 to Membrane Bound FGFR-3

Clone cDNA of murine FGFR-3(IIIc) into a pBABE expression vector containing the puromycin selection gene. Perform retroviral expressions of resulting plasmids in L6 cells. Cells are selected and cultured in DMEM medium containing 10% FBS and 2 μg/ml puromycin. Suspend the FGFR-3 expressing L6 cells in 1% BSA/PBS. Add Antibody 1 to the final concentrations of 1-30 μg/ml. After a 1-hour incubation on ice, wash cells in 1% BSA/PBS and incubate with an appropriate secondary detecting antibody or Fab fragments in the same buffer for 1 hour on ice. Stain control samples only with this secondary antibody. Analyze all samples using a FACSvantage SE flow cytometer (BD Biosciences). Antibody 1 is specific to FGFR-3 as shown by producing positive staining signals only when FGFR-3-transfected cells (R3-L6) are used, but not when the FGFR-3 negative L6 parental cells are used.

Human embryonic kidney (HEK) 293 cells, 293 fectin, FreeStyle 293 Medium and OptiMEM Medium may be purchased from Invitrogen (Carlsbad, Calif.). Protein-A affinity purification media may be purchased from GE Healthcare. Generate a DNA construct for FGFR(IIIb)-Fc.

Production of FGFR-3(IIIb)-Fc, FGFR-3(IIIb)-Fc Ig Domain Truncates, and Single Residue Alanine Mutants of FGFR-3 (IIIb)-Fc.

FGFR-3(III)b domain boundaries may be defined based on the FGFR-3(IIIb) extracellular domain 3D model as well as the crystal structures of the FGFRs, which are known. Five truncated FGFR-3(IIIb) ECD constructs are designed, namely D1 (25-148), D2 (149-245), D3 (250-372), D1-2 (25-245) and D2-3 (149-372) along with wild-type FGFR-3 (IIIb) D1-3 (25-372). The constructs are subcloned into a pGS vector with a Fc tag engineered at the 3' end of the multiple cloning site and the sequences confirmed. Twenty FGFR-3 (IIIb) residues in proximity to the putative ligand binding region, as well as those implicated in heparin binding and receptor-receptor dimerization are selected based on the FGFR-3(IIIb) ECD model and the FGFR-3(IIIc) structure as known. FGFR-3(IIIb) ECD single residue alanine mutants are generated via overlapping PCR using the full length FGFR(IIIb) ECD construct as the template, and subsequently subcloned into the pGS-Fc vector. The domain truncates and alanine mutants are expressed transiently in 293 cells following transfection using 293 Fectin™ (Invitrogen). Culture supernatants are harvested 6 days post-transfection and Fc containing the proteins are purified by passage over a protein-A affinity column, buffer exchanged into PBS, quantitated and evaluated by SDS-PAGE analysis to confirm structural integrity.

FGFR-3(IIIb)-Fc Mesoscale binding assay: A purified solution of Antibody-1 is diluted to a concentration of 2 mg/ml in PBS. MSD Sulfo-TAG NHS-Ester (MesoScale Discovery, #R91AN2), a ruthenium-tris-bipyridine N-hydroxysuccinimide ester, is reconstituted with cold distilled water to a concentration of 10 nmol/ul. A 12:1 molar ratio of MSD Sulfo-TAG NHS-Ester to Antibody 1 is used for the reaction. Incubations are performed at room temperature, protected from light, for 2 hours. The unreacted MSD Sulfo-TAG NHS-Ester is removed from the conjugated Antibody 1 using a desalting resin. Ruthenium conjugated Antibody 1 is stored at −80° C. Concentration of the conjugated Antibody 1 is determined using bovine serum albumin for the standard curve.

Truncated, mutant or wild type FGFR-3(IIIb)-Fc is diluted in phosphate buffered saline PBS to 5 µg/mL. Standard 96 well plates are coated with 25 ng/well of receptor and incubated for 1 hr at room temperature. To block non-specific binding in the wells, 150 µL of 5% MSD Blocker A (MesoScale Discovery, #R93Ba-1) is added to each well. The plates are incubated for 1 hr at room temperature. Blocking solution is removed and plates are washed five times with 200 µL of PBS, pH 7.4, 0.02% Tween®-20. A three-fold dilution series (250–0.001 nM) of the ruthenium-labeled Antibody 1 is added in a volume of 25 µL in triplicate for each protein being tested. After a one hour incubation at room temperature with mild agitation and protected from light, free ruthenium-labeled antibody is removed by performing another five washes with PBS, pH 7.4, 0.02% Tween-20, 200 µL per well. After this wash, 150 µL of 1× read buffer (MesoScale Discovery, #R92TC-2) is added to each well. Upon electrochemical stimulation, ruthenium label on the bound antibody emitted luminescent light at 620 nm. Electrochemiluminescence ECL signals are detected by a charge-coupled device camera in a SECTOR Imager 2400 plate reader (MesoScale Discovery, #1250) and expressed as ECLU. ECL signals are plotted in GraphPad Prism software version 5.0. KD values are calculated by nonlinear regression curve fit analysis of the software's One Site—Specific Binding function. Binding of ruthenium-labeled Antibody 1 to wild type FGFR-3(IIIb)-Fc is used as a standard for the relative binding affinity analysis of the truncated or mutant FGFRs, plotted as a percentage of the wild type.

Mab B9 ELISA binding assay: The wells of a 96 well ELISA microtiter plate are coated overnight with 200 n g of an anti-FGFR-3 monoclonal antibody, B9 (Santa Cruz sc-13121), in 100 µL of PBS, pH 7.2 with mild agitation at 4° C. After coating, the antibody solution is decanted and the wells are blocked with 100 µL of phosphate buffer saline with 0.1% Tween (PBST), 5% Bovine serum albumin (BSA) for 2 hours at room temperature with mild agitation. After blocking, the wells are washed 5 times with 200 µL PBST. A three-fold dilution series (100–0.006 nM) of the mutant or wild type FGFR-3(IIIb)-Fc is then added in 100 µL of PBST, 1% BSA in triplicate for each protein being tested and incubated with mild agitation for 1 hour at room temperature. The wells are washed again 5 times with 200 µL PBST. A 1:5000 dilution of horse radish peroxidase (HRP)-conjugated anti-mouse IgG in 100 µL of PBST, 5% BSA is incubated in each well for 1 hour at room temperature with mild agitation. The wells are washed a final 5 times with 200 µL PBST then developed with 100 µL of 3,3',5,5'-Tetramethylbenzidine peroxidase (TMB) chromogenic substrate for 5 minutes. The reaction is stopped with 100 µL of 1N $H_2SO_4$ per well. Absorbance is measured spectrophotometrically at 450 nm. Absorbance readings are plotted in GraphPad Prism® software version 5.0. KD values are calculated by nonlinear regression curve fit analysis of the software's One Site—Specific Binding function. Binding of B9 to the wild type FGFR-3(IIIb)-Fc is used as a standard for the relative binding affinity analysis of the truncate or mutant FGFRs, plotted as a percentage of the wild type.

Molecular modeling of human FGFR-3(IIIb): To help guide the mutagenesis studies, a three-dimensional model of the domains 2 and 3 of the FGFR-3(IIIb) ECD is generated using SWISS-MODEL®. The sequences of human FGFR-3 (IIIb), and human FGFR-3(IIIc) are aligned using the CLUSTALW® method, and the model is constructed using the X-ray crystal structure of FGFR-3(IIIc) as the template (Protein Data Bank code 1RY7).

The epitope of Antibody 1 is contained within the second immunoglobulin-like (Ig) domain of FGFR-3: The ligand-binding sites of the FGFR receptor family are contained within the three N-terminal Ig domains which define the extracellular domain (Chellaiah, et al., J. Biol. Chem. 1999 Dec. 3; 274(49):34785-34794). To determine which of the three Ig domains contains the epitope of Antibody 1, a panel of domain truncates is employed. DNA sequences encoding the human Ig domains are truncated in various forms and expressed as homodimeric fusion proteins with human Fc tags. The encoded proteins are purified from conditioned supernatant of transiently transfected cells and the homodimeric structure of each purified domain truncate is confirmed by SDS-PAGE. The truncates are then tested for binding to Antibody 1 in a mesoscale binding assay (Meso Scale Discovery, Gaithersburg, Md.). While Antibody 1 showed no detectable binding to truncates D1 and D3, it showed significant binding to truncates D1-2 and D2 as determined in a mesoscale binding assay (Meso Scale Discovery, Gaithersburg, Md.) and by BIAcore™ (Pharmacia, Piscataway, N.J.). B9 recognizes a conformationally sensitive epitope in domain 1 of the receptor therefore those truncates containing domain 1 would be expected to bind the antibody if the overall structure was not disturbed. The D1 and D1-2 truncates showed significant binding to control Mab B9, confirming the structural integrity of those two proteins as determined in a mesoscale binding assay (Meso Scale Discovery, Gaithersburg, Md.) and by BIAcore™ (Pharmacia, Piscataway, N.J.). The truncate binding data revealed that the second Ig domain of FGFR-3 is sufficient for binding Antibody 1 and thus contains residues critical to the epitope.

Identification of amino acids of FGFR-3 within the epitope recognized by Antibody 1: A three-dimensional model of the domains 2 and 3 of the FGFR-3(IIIb) ECD was generated based on the crystal structure of FGFR-3(IIIc). Twenty amino acids (D160, K161, K162, L163, L164, V166, P167, P220, R223, D244, N170, T171, R158, R173, R175, K205, R207, L246, E247, S249) within the second domain of FGFR-3 that are in proximity to or directly involved in ligand binding, receptor dimerization or heparin binding are identified based on the molecular model and single residue alanine mutations are generated.

The wild-type sequence of FGFR-3 domain 2 is determined (SEQ ID NO 12). Each amino acid indicated is mutated individually to alanine by site-directed mutagenesis and expressed in the context of FGFR(IIIb)-Fc protein encoding the full ECD. The encoded mutant proteins are purified from conditioned supernatant of transiently transfected cells and the homodimeric structure of each purified mutant is confirmed by SDS-PAGE.

A residue is considered critical to the epitope if the alanine mutation described above leads to a significant loss of binding to Antibody 1. All mutant proteins that show significant loss of binding are then tested for binding to Mab B9 to check for gross changes in overall protein structure. Of the 20 positions examined, the substitution of Alanine for Arginine at position 173 (R173A) leads to almost complete loss of binding to Antibody 1 (>90% decrease of binding compared to WT); whereas the other substitutions retained binding (<20% decrease of binding compared to WT). Subsequent testing showed that binding to Mab B9 was not affected by the R173A substitution, suggesting that position 173 constitutes a critical residue for the specific recognition of the receptor by Antibody 1. The affinity of Antibody 1 for the R173A mutant is determined by BIAcore® analysis. The binding of Antibody 1 to the R173A mutant is 7-fold poorer than the affinity of the antibody for the wild-type protein.

Sequence comparison reveals that the Arginine residue at position 173 of the human and mouse FGFR-3 sequences is not shared by the other family members, suggesting that this residue is likely responsible for the FGFR-3 specificity exhibited by Antibody 1.

FGFR-3 Antibody Antagonist Blocks FGFR-3(IIIb) and FGFR-3(IIIc)-Mediated FGF Binding and Cell Signaling Results from the aforementioned ELISA blocking assay show that Antibody 1 blocks FGF-1/FGFR-3 binding with an IC50 within the range of 1-10 nM. Use FGFR-3 expressing L6 cells described above to test the activities of this antibody on FGFR-3 signaling in live cells. Quiesce the FGFR-3 expressing L6 cells overnight in media with very low concentration of serum (0.1%). The next day divide cells into five samples of equal size. Treat sample 1 and 2 for 1 h with an isotype-matched non-specific control antibody (200 nM) and Antibody 1 (200 nM), respectively. Expose samples 3 for 15 min with 0.6 nM of FGF-9. Treat samples 4 and 5 first for 1 h with an isotype-matched non-specific control antibody (200 nM) and Antibody 1 (200 nM), respectively, then expose for 15 min with 0.6 nM of FGF-9. After these treatments and exposures, lyse the cells and subject them to SDS-PAGE and western blot. Probe for the activation of FGFR-3 with an anti-phospho-Tyrosine antibody. Antibody 1 alone neither increased nor decreased the signals of activated FGFR-3 and MAPK, and FGF-9 ligand exposure increases the signals of activated FGFR-3 and MAPK to the same degree. These results thus demonstrate that Antibody 1 is an antagonist that blocks the FGFR-3 receptor in ligand-induced activation in live cells.

Cell Surface FGFR-3 is Internalized Upon Binding to Antibody 1.

Antibody 1 triggers the internalization of FGFR-3, constituting a mechanism of down-modulating the receptor signaling. To test this, label the antibody with the commercially available Alexa Fluor® dye (Invitrogen). In order to trace the location of the Antibody 1/FGFR-3 complex. Conjugate Antibody 1 and an isotype matched nonspecific control antibody with the fluorescent dye. Quiesce the FGFR-3 expressing L6 cells overnight in media with very low concentration of serum (0.1%).

Divide the cells into 8 samples of equal size and seed into wells of a 6-well tissue culture plate. These samples are subjected to three distinct procedures: 1) Binding, in which cells are incubated with 1 mL of 200 nM conjugated antibodies for 1 h at 4° C. The temperature is prohibitory low for endocytosis but conducive to antibody-antigen interaction; 2) Internalizing, in which cells are incubated with 1 mL of 200 nM conjugated antibodies for 1 h at 37° C. This temperature will allow endocytosis; 3) Stripping, in which cells are treated with 1 mL of 0.2 M glycine-0.15 M NaCl, pH3 for 30 min at 4° C. In this condition, antibodies that are not internalized can no longer bind to the surface receptor and are released into the media. The eight FGFR-3 transfected L6 cell samples are treated according to the following description: Sample 1 is incubated with the conjugated control antibody (200 nM, 1 mL) for 1 h at 4° C.; Sample 2 is incubated with the conjugated control antibody (200 nM, 1 mL) for 1 h at 4° C., followed by stripping; Sample 3 is treated with the conjugated control antibody (200 nM, 1 mL) for 1 h at 37° C.; Sample 4 is treated with the conjugated control antibody (200 nM, 1 mL) for 1 h at 37° C. followed by stripping; Sample 5 is treated with conjugated Antibody 1 (200 nM, 1 mL) for 1 h at 4° C. Sample 6 is treated with conjugated Antibody 1 (200 nM, 1 mL) for 1 h at 4° C. followed by stripping; Sample 7 is treated with conjugated Antibody 1 (200 nM, 1 mL) for 1 h at 37° C. Sample 8 is treated with conjugated Antibody 1 (200 nM, 1 mL) for 1 h at 37° C. followed by stripping. After these treatments, all cells are washed three times with 1 mL of ice-cold PBS and subject to the Odyssey Infrared Imaging system for the detection of relative fluorescent intensity. The readouts of sample 1-8 are as follows: 1.5, 0.6, 1.1, 1, 3.3, 1.5, 5, and 5.8. The conditions under which Samples 1 and 5 are treated allows antibody-cell surface binding but not internalization. The conditions under which Samples 2 and 6 are treated allow neither cell-surface binding nor internalization. The conditions under which Samples 3 and 7 are treated allow cell-surface binding and internalization. The conditions under which Samples 4 and 8 are treated allows internalization but not cell-surface binding. The signals generated by Samples 1-4, as well as Sample 6 are considered background due to non-specificities.

Perform an "acid wash" step on some samples following the incubation to strip off surface-bound antibodies without affecting those that had been trafficked inside the cells. This enables the quantification of internalized antibodies. A similarly labeled control antibody (non-specific hIgG) is not retained regardless of incubation temperature or the washing step. Although Antibody 1 is retained at both temperatures before the wash, only those incubated at 37° C. remain afterward; demonstrating the internalization of the antibody by the cells.

Antibody 1 Induces FGFR-3 Receptor Degradation in Cells.

OPM-2 is a cell line originally isolated from cancer cells of multiple myeloma. OPM-2 cells are known to express FGFR-3 receptors harboring a gain-of-function K650E point mutation. Quiesce the OPM-2 cells in low serum culture media (0.1% FBS) for overnight. The next day, divide these cells into 5 groups. Group 1 is lysed immediately, and the lysate is kept at −20° C. until the time of western blot analysis. This group is therefore designated as Time 0 hr sample. Group 2-5 each has 3 samples of equal size, named as Sample A, B and C of Group 2, 3, 4, and 5. Samples A of Group 2-5 are not subjected to any further treatment, but are incubated at 37° C. Samples B of Group 2-5 are treated with 30 ng/ml FGF-1 at 37° C. Samples C of Group 2-5 are treated with 30 ug/ml Antibody 1 at 37° C. All samples of Group 2 are lysed after 1 hr of treatment, and the lysates are kept at −20° C. until the time of western blot analysis. This group is designated as the Time 1 hr samples. All samples of Group 3 are lysed after 4 hr of treatment, and the lysates are kept at −20° C. until the time of western blot analysis. This group is designated as the Time 4 hr samples. All samples of Group 4 are lysed after 8 hr of treatment, and the lysates are kept at −20° C. until the time of western blot analysis. This group is designated as Time 8 hr samples. All samples of Group 5 are lysed after 24 hr of treatment, and the lysates are kept at −20° C. until the time of western blot analysis. This group is designated as Time 24 hr samples. When all lysates are ready, they are subjected to SDS-PAGE followed by Western Blot experiment. The FGFR-3 signals of Group 1 and all samples of Group 2 are similar. In Group 3, FGFR-3 signals of Samples A and C are similar to that of Group 1; yet signal of Sample B is significantly lower. In Group 4, the FGFR-3 signal of Sample A is similar to that of Group 1; yet signals of Samples B and C are significantly lower. In Group 5, the FGFR-3 signal of Sample A is lower than that of group 1; yet signals of Samples B and C are nearly absent. Therefore, similar to FGF-1, which is known to induce FGFR degradation, Antibody 1 is capable of inducing FGFR-3 degradation in a time-dependent manner; a feature that we believe has not been shown to date.

Antibody 1 Induces Depletion of Mutant FGFR-3 Receptor from Cell Surface

Most FGFR-3-activating mutations identified in bladder cancer are located in the extracellular domain of the receptor. These mutations (e.g. R248C or S249C) give rise to a new, unpaired cysteine residue, leading to formation of disulfide-linked FGFR-3 dimers in a ligand-independent manner. The most frequent mutations are S249C, Y375C and R248C, which together account for 91% of all FGFR-3 mutations in bladder cancer. In addition, S249C on FGFR-3(IIIc) also leads to constitutive activation of FGFR3(IIIc). Antibody 1 can internalize and deplete not only wild type (WT) FGFR-3, but also the most prevalent tumor-associated FGFR-3 mutants.

To generate NIH-3T3 and Ba/F3 cell lines stably expressing each of the three most common FGFR3 mutant variants and the WT FGFR-3, clone cDNA encoding full-length human FGFR-3(IIIb) or (IIIc) into pMSCVpuro retraviral vector (Clontech Laboratories, Mountain View, Calif.) to generate pMSCVpuro-FGFR-3(IIIb) or (IIIc). Specific mutations, i.e., S249C, Y375C and R248C, are introduced into the cDNA via QickChange (Stratagene, La Jolla, Calif.). To generate NIH3T3 and Ba/F3 stable cells expressing WT or mutant FGFR-3, various pMSCVneo constracts are transfected into packaging cells Phoenix-Eco (ATCC, Manassas, Va.) with Lipofectamine (Invitrogen). The retrovirus are collected and used to infect NIH-3T3 and Ba/F3 cells. After selection with 2 µg/µl puromycin for two weeks, cell expressing WT or mutant FGFR-3 are stained with Alexa Fluor 488-conjugated anti-human FGFR-3 and analyzed using fluorescence-activated cell sorting (FACS).

For Antibody 1-induced internalization/depletion of mutant and WT FGFR-3 from cell surface, wells of 6-well tissue culture plates (Costar, #3598) are seeded with $1.5 \times 10^5$ NIH-3T3-FGFR-3 mutant in 2 mL of culture medium (DMEM (Invitrogen); 10% (v/v) FCS (Invitrogen); 2 mM L-glutamine (Invitrogen); 100 U/500 mL penicillin G, and 100 µg/500 mL streptomycin (Invitrogen)). The plates are incubated for 24 hours at 37° C. under 95% relative humidity and 5% (v/v) $CO_2$. Antibody 1 is then added to the wells at a final concentration of 5 µg/mL. After 2-hour treatment, the culture medium is removed from the wells and replaced with 1 mL of enzyme-free cell dissociation solution (Chemicon, #S-014-B). The cells are collected into centrifuge tubes after being incubated for 5 min. at room temperature, and washed once in culture medium followed by one more wash in binding buffer (DPBS with 1% (w/v) BSA and 0.01% (w/v) sodium azide). Before staining cells, an FGFR-3 antibody that recognizes a different epitope from Antibody 1 is labeled by using an Alexa Fluor 488 Monoclonal Antibody Labeling Kit (Molecular Probes, Eugene, Oreg.) according to the supplier's instructions. 100 µL of binding buffer containing 2 µg/mL of the Alexa Fluor 488-labeled antibody are added to the cells, which are then incubated for 60 min. on ice. The cells are then washed once with binding buffer and resuspended in DPBS containing 2 µg/mL propidium iodide (to stain the dead cells). The amount of FGFR-3 molecules remaining on the cell surface is analyzed by FACS analysis, and 10,000 events are acquired for each sample.

The mean fluorescence intensity on the cell surface reflects the quantity of FGFR-3 molecules that remain on the cell surface after treatment with Antibody 1. The percentage of depletion of FGFR-3 on the cell surface is calculated by using the mean fluorescence intensity of Antibody 1 treated cells divided by the mean fluorescence intensity of human IgG1 treated cells. Antibody 1 significantly reduced both WT and mutant FGFR-3 from cell surfaces.

For the Ba/F3-FGFR3 cell proliferation assay, 80,000 cells/well are seeded in RPMI 1640 medium supplemented with 10% FBS. Antibody 1 is added at a concentration of 0.005 to 10 ug/ml with heparin (StemCell Technologies, Vancouver, Canada). After incubation for 72 hrs, cells were pulsed with 20 ul (2 uCi)/200 ul of methyl-3H thymidine for 6 hours at 37° C., 5% CO2. The cells were harvested and counted for 3H thymidine incorporation. Antibody 1 significantly inhibited Ba/F3-FGFR-3-R248C proliferation.

FGFR-3 Antibody Antagonist Inhibits FGF-Signaling in FGFR-3 Expressing Tumor Cells In Vitro.

Identify tumor cell lines that express wild type or mutant FGFR-3 (IIIb and/or IIIc) using flow cytometry in which Antibody 1 is the primary antibody. Three bladder tumor cell lines, RT112, RT4 and BFTC905 show significant FGFR-3 expression. OPM-2 cells, known to express FGFR-3 receptors harboring a gain-of-function K650E point mutation, also display high level of expression in this study. Two additional cell lines, GEO and FADU, are found to express moderate but still significant levels of the receptor. The FGFR-3 signaling pathway in these tumor cells is characterized using western blot.

OPM-2 is a cell line derived from human multiple myeloma tumors. Quiesce the cells in low serum culture media (0.1% FBS) overnight. The next day, divide these cells into four samples of equal size. Set aside and keep sample 1 at 37° C. for 1 h as the control sample. Incubate sample 2 with 200 nM of Antibody 1 at 37° C. for 1 h. Set aside sample 3 at 37° C. for 1 h, then expose the same sample with 0.2 nM of FGF-9 ligand at 37° C. for 15 min. Incubate sample 4 with 200 nM of Antibody 1 for at 37° C. for 1 h, then expose the same sample with 0.2 nM of FGF-9 at 37° C. for 15 min. Next, lyse all four samples and subject them to SDS-PAGE followed by Western blotting. Probe the activation of FGFR-3 with an anti-phospho-Tyrosine antibody. Probe the activation of down-stream effector molecule MAPK with an anti-phospho-MAPK antibody. Probe the activation of down-stream effector molecule Akt with an anti-phospho-Akt antibody. The signals of phosphor-FGFR-3 from Samples 2 and 4 are comparable to that from Sample 1, which represents the un-stimulated state of the receptor. The signal of Sample 3 is more than tripled that of Sample 1. It can be concluded that Antibody 1 antagonizes the effect of FGF-9 on FGFR-3 activation. The signals of phosphor-MAPK from Samples 2 and 4 are comparable to that from sample 1, which represented the un-stimulated state of the receptor. The signal of Sample 3 is more than doubled that of Sample 1. It can be concluded that Antibody 1 antagonizes the effect of FGF-9 on MAPK activation. GEO is a cell line derived from human colorectal tumors. Quiesce the cells in low serum media (0.1% FBS) overnight. The next day, divide these cells into six samples of equal size. Set aside and keep sample 1 at 37° C. for 1 h as the control sample. Incubate sample 2 with 200 nM of 200 nM isotype-matched non-specific control antibody at 37° C. for 1 h. Incubate sample 3 with 200 nM of Antibody 1 at 37° C. for 1 h. Set aside sample 4 at 37° C. for 1 h, then expose the same sample with 0.67 nM of FGF-1 ligand at 37° C. for 15 min. Incubate sample 5 with 200 nM control antibody for at 37° C. for 1 h, than expose the same sample with 0.67 nM FGF-1 at 37° C. for 15 min. Incubate sample 6 with 200 nM Antibody 1 for at 37° C. for 1 h, than expose the same sample with 0.67 nM FGF-1 at 37° C. for 15 min. Lyse all six samples and subject them to SDS-PAGE followed by Western blotting. Probe the activation of FGFR-3 with an anti-phospho-Tyrosine antibody. Samples 1, 2 and 4 have similar low levels of phosphor-FGFR-3, whereas sample 3 alone has significantly higher signals corresponding to all three kinds of molecules. Therefore, 1) FGF-9 exposure increases phosphorylation of FGFR-3; 2) Antibody 1 antagonizes these increases, and 3) Antibody 1 alone does not have any agonist activity.

RT-112 is a cell line derived from human bladder tumors. Quiesce the cells in low serum culture media (0.1% FBS) for overnight. The next day, divide these cells into four samples of equal size. Set aside and keep sample 1 at 37° C. for 1 h as the control sample. Incubate sample 2 with 200 nM of Antibody 1 at 37° C. for 1 h. Set aside sample 3 at 37° C. for 1 h, then expose the same sample with 1.3 nM of FGF-1 ligand at 37° C. for 15 min. Incubate sample 4 with 200 nM of Antibody 1 for at 37° C. for 1 h, then expose the same sample with 0.13 nM of FGF-1 at 37° C. for 15 min. Next, lyse all four samples and subject 10% of each lysed sample to SDS-PAGE followed by Western blotting. Probe the activation of down-stream effector molecule MAPK with an anti-phospho-MAPK antibody. Probe the activation of down-stream effector molecule Akt with an anti-phospho-Akt antibody. Subject the other 90% of each lysate to an immunoprecipitation experiment. Mix the sample with a commercial anti-FGFR-3 antibody at 4° C. for 4-16 hrs to allow the antibody to collect the FGFR-3 receptors in the lysates, and then retrieve the anti-FGFR-3 antibody-bound FGFR-3 by mixing 20 μg of protein A-protein G beads mixture (50:50, V:V) to the samples at 4° C. for overnight. Wash these beads 3 times with PBS, before subjecting them to SDS-PAGE and Western blotting. Probe the activation of FGFR-3 with an anti-phospho-Tyrosine antibody. Samples 1, 2 and 4 have similar low levels of phosphor-FGFR-3 and phosphor-MAPK, whereas sample 3 alone has significantly higher signals corresponding to all three kinds of molecules. Therefore, 1) FGF-1 exposure increases phosphorylation of FGFR-3, and MAPK; 2) Antibody 1 antagonizes these increases, and 3) Antibody 1 alone does not have any agonist activity. Sample 4 alone has lower phosphor-Akt signal than the rest, indicating that Antibody 1 may antagonize Akt signaling as well.

Use GEO cells to prepare the six samples described above, then lyse and subject them to SDS-PAGE followed by Western blotting as above. However, probe the activation of downstream effector molecule MAPK with an anti-phospho-MAPK antibody. Probe the activation of down-stream effector molecule Akt with an anti-phospho-Akt antibody. Samples 1, 2, 3 and 6 have similar low levels of phosphor-MAPK, whereas Samples 4 and 5 have significantly higher signals corresponding to all three kinds of molecules. Therefore, 1) FGF-1 exposure increases phosphorylation of MAPK; 2) Antibody 1 antagonizes this increases, and 3) Antibody 1 alone does not have any agonist activity.

Antibody 1 Inhibits Tumor Cell Growth and Survival In Vitro

A cell proliferation assay is used to show the inhibitory effects of Antibody 1 on the growth of tumor cells. Quiesce monolayer RT112 cells in low serum culture media (0.1% fetal bovine serum, 5 μg/mL heparin) for 24-72 hrs. Divide cells into 4 samples. Add FBS (Fetal Bovine Serum) to Sample 1 to the final concentration of 10% (V:V). Leave Sample 2 in the starving media. Add FGF-1 to Sample 3 to the final concentration of 1 nM. Add Antibody 1 to Sample 4 to the final concentration of 200 nM, incubate at 37° C. for 1 hr. Next, add FGF-1 to the final concentration of 1 nM. After preparing Samples 1-4 as described above, incubate the samples in a tissue culture incubator set at 37° C. and with 5% $CO_2$ (v:v) for 48 hours. Detect cell growth using standard $^3$H-thymidine incorporation, assays. Tumor cell growth is doubled when RT112 cells in vivo are stimulated with 1 nM exogenous FGF-1. The experiment also shows that Antibody 1 effectively reduces this exogenously stimulated growth.

A soft agar assay, also known as colony formation assay or colonigenic assay, is used to show the inhibitory effects of Antibody 1 on the survival of tumor cells. RT112 cells grown in soft-agar containing 200 nM Antibody 1 (in 10% FBS culture media) form ~50% few colonies than those grown in soft-agar containing 10% FBS culture media alone, or containing 200 nM isotype-matched nonspecific control antibody (in 10% FBS culture media). This shows the anti-survival effects of Antibody 1 on the tumor cells.

Antibody 1 Shows Anti-Tumor Effects on FGFR-3-Bearing Solid Tumors.

Develop RT112 and GEO xenograft tumor models by routine methods in which 1-20 million tumor cells mixed with 0-100% Matrigel are injected subcutaneously to each female athymic nude mouse. Start antibody treatment once the mean volume of the subcutaneous tumors is approximately 400 mm$^2$. The two tumor cell lines RT112 and GEO corresponding xenograft tumors both are effectively inhibited by the three times weekly 40 mg/kg Antibody 1 i.p. injection treatment compared to the same type of tumors in the control cohorts. To demonstrate that these effects are emanated from the rendering of the FGFR-3 signaling pathway, conduct an efficacy study using a Orthotopic PC-3 tumor model in which the tumor cells are devoid of FGFR-3 signaling as suggested by the negative results from a Western Blot analysis of the FGFR-3 receptor phosphorylation. Orthotopic PC-3 model was generated by injecting luciferase transfected PC-3 cells (PC-3LP) directly into the dorsal lobe prostates of Nu/nu mice (male, 7-8 weeks, 1×10$^6$ cells/mouse) through surgery. Two weeks after cell implantation, bioluminescence images of the animals are captured in the ventral position (animals laying on back) and quantified using the IVIS system according to manufacturer's instructions (Caliper Life Sciences, Hopkinton, Mass.). Mice with successful implants are randomized into groups to receive various testing agents i.p. on a predetermined schedule. Signals captured by IVIS are used as surrogates of tumor burden, and are recorded weekly. Statistical analyses are performed using repeated ANOVA. Antibody 1 shows no significant effect on the growth of the PC-3 tumors. Therefore Antibody 1 inhibits the growth of those solid tumors that possess functional FGFR-3 signaling pathways.

Antibody 1 Shows Anti-Tumor Effect on Myeloid Tumors with Mutant FGFR-3 Receptors OPM-2 and KMS-11 are FGFR-3 expressing multiple myeloma cell lines. In addition, receptors in both cell lines are mutants harboring single point-mutations: K650E in OPM-2 and Y373C in KMS-11. The two mutations are gain-of-function mutations and heighten the activity of the mutant receptors through mechanisms such as constitutive activation, prolonged half-life and increased ligand sensitivity. Develop an OPM-2 xenograft model by routine methods in which 1-20 millions of tumor cells mixed with 0-100% Matrigel are injected subcutaneously to each female athymic nude mouse. Start injection treatment once the mean volume of the subcutaneous tumors is approximately 400 mm$^2$. Treat 3 times weekly. Measure tumor volumes 3 times weekly. Make final measurement after 4 weeks of treatment. Mean tumor size of the Antibody 1 treated animals is 64% smaller than that of the control group. Perform Student t-test. The P value is less than 0.0001. Therefore the finding is highly significant. A KMS-11 bone engraftment model is established according to Xin X, et al., Clin Cancer Res. 2006 Aug. 15; 12(16):4908-15. Start antibody treatment 1 week after the tumor cell injections. Treat 3 times weekly. Measure signals emitted by the tumor cells several times during the study. Make final measurement after 33 days after the first injection. Mean signal from Antibody 1 treated animals is ¼ of that from the control animals. Conduct Long-rank (Mantel-Cox) Test. The P value is 0.0002. Therefore the finding is highly significant. In both models, three times weekly 40 mg/kg Antibody 1 i.p. injections treatment significantly inhibits tumor growth compared to the control cohorts. Antibody 1 appears to be the first to demonstrate in vivo anti-tumor activity against tumor cells that possess K650E as well as those that possess Y373C mutant forms of FGFR-3.

Antibody 1 Enhances the Therapeutic Efficacy of Cytotoxic Agents.

Cisplatin is a widely used cytotoxic agent in cancer therapies. It causes DNA cross-linking and induces cell apoptosis. The therapeutic benefit of combining cisplatin with FGFR-3 antibody in three bladder xenograft models is explored. Develop RT112, RT4 and BFTC905 xenograft tumor models by routine methods in which 1-20 million tumor cells mixed with 0-100% Matrigel are injected subcutaneously to each female athymic nude mouse. Start antibody treatment once the mean volume of the subcutaneous tumors is approximately 400 mm$^2$. Use 40 mg/kg three times weekly injections of Antibody 1 and the maximal-tolerated-dose (MTD) of cisplatin. Measure tumor volumes 3 times weekly until the end of the studies. A summary of the data of RT112 tumor model are recorded in the following table:

TABLE 3

Individual RT-112 Tumor Volumes (mm$^3$) - Cisplatin Treatment

| Treatment | Day 1 | Day 8 | Day 15 | Day 22 | Day 29 | Day 36 | Day 42 |
|---|---|---|---|---|---|---|---|
| USP Saline Average | 181.2 | 288.7 | 560.6 | 909.9 | 1346.4 | 1758.6 | 2211.0 |
| ±S.E.M. | 9.0 | 18.3 | 33.5 | 79.5 | 133.5 | 177.4 | 224.7 |
| Antibody 1 Average | 180.6 | 260.3 | 398.2 | 655.3 | 926.4 | 1217.9 | 1501.9 |
| ±S.E.M. | 8.8 | 22.2 | 41.7 | 44.2 | 81.5 | 124.2 | 163.7 |
| Cisplatin Average | 175.7 | 245.1 | 360.8 | 578.8 | 739.4 | 881.6 | 1115.9 |
| ±S.E.M. | 9.1 | 14.1 | 32.1 | 67.8 | 87.8 | 139.2 | 202.3 |
| Antibody 1 + Cisplatin Average | 188.2 | 236.0 | 327.6 | 488.3 | 517.0 | 539.7 | 501.8 |
| ±S.E.M. | 10.1 | 17.0 | 31.3 | 57.9 | 82.9 | 98.5 | 103.6 |

Conduct RM ANOVO statistical test. Compare the efficacy of cisplatin treatment vs. that of cisplatin-Antibody 1 combination. P value is 0.018. Therefore the effect of Antibody 1 on the increased efficacy of cisplatin is highly significant.

A summary of the data of RT4 tumor model are recorded in the following table:

TABLE 4

Individual RT4 Tumor Volumes (mm$^3$) - Cisplatin Treatment

| Treatment | Day 1 | Day 8 | Day 15 | Day 22 | Day 29 | Day 36 | Day 42 |
|---|---|---|---|---|---|---|---|
| USP Saline Average | 186.0 | 314.9 | 624.5 | 899.6 | 1351.9 | 1813.2 | 2441.2 |
| ±S.E.M. | 9.0 | 26.2 | 43.9 | 58.7 | 104.6 | 194.2 | 270.0 |
| Antibody 1 Average | 209.1 | 289.8 | 500.9 | 670.6 | 913.0 | 1163.6 | 1496.0 |
| ±S.E.M. | 12.2 | 19.5 | 42.0 | 75.0 | 117.4 | 136.9 | 186.9 |
| Cisplatin Average | 195.4 | 253.4 | 374.0 | 511.9 | 675.8 | 840.5 | 1024.5 |
| ±S.E.M. | 9.5 | 16.5 | 38.9 | 70.4 | 80.3 | 119.0 | 171.0 |
| Antibody 1 + Cisplatin Average | 199.5 | 264.2 | 346.2 | 414.8 | 429.8 | 481.7 | 527.6 |
| ±S.E.M. | 9.4 | 20.2 | 43.0 | 45.5 | 72.8 | 109.2 | 145.4 |

Conduct RM ANOVO statistical test. Compare the efficacy of cisplatin treatment vs. that of cisplatin-Antibody 1 combination. P value is 0.0162. Therefore the effect of Antibody 1 on the increased efficacy of cisplatin is highly significant.

A summary of the data of BFTC905 tumor model are recorded in the following table:

TABLE 5

Individual BFTC-905 Tumor Volumes (mm$^3$) - Cisplatin Treatment

| Treatment | Day 0 | Day 3 | Day 7 | Day 14 | Day 21 | Day 28 | Day 35 | Day 42 |
|---|---|---|---|---|---|---|---|---|
| USP Saline Average | 189.0 | 239.4 | 285.3 | 470.3 | 756.9 | 1227.3 | 1812.8 | 2649.5 |
| ±S.E.M. | 11.1 | 17.0 | 20.5 | 57.8 | 76.7 | 134.3 | 225.9 | 367.5 |
| Antibody 1 Average | 191.9 | 220.5 | 252.3 | 334.2 | 527.2 | 727.7 | 932.5 | 1346.8 |
| ±S.E.M. | 11.9 | 18.0 | 18.3 | 27.8 | 52.4 | 77.5 | 104.1 | 187.9 |
| Cisplatin Average | 192.1 | 211.4 | 243.4 | 286.7 | 395.0 | 511.6 | 615.5 | 829.6 |
| ±S.E.M. | 14.2 | 15.3 | 18.7 | 33.9 | 56.6 | 81.2 | 116.9 | 165.1 |
| Antibody 1 + Cisplatin Average | 212.1 | 225.9 | 237.1 | 275.3 | 280.0 | 311.6 | 311.4 | 331.4 |
| ±S.E.M. | 12.6 | 16.2 | 21.7 | 22.1 | 52.1 | 81.2 | 97.7 | 137.6 |

Conduct RM ANOVO statistical test. Compare the efficacy of cisplatin treatment vs. that of cisplatin-Antibody 1 combination. The P value is 0.0209. Therefore the effect of Antibody 1 on the increased efficacy of cisplatin is highly significant.

None of the animals died of the treatments during the entire courses of these studies, suggesting that adding Antibody 1 to MTD of cisplatin enhances the efficacy of the latter without significantly worsening the adverse effects of the two drugs.

We claim:

1. A method of treating bladder cancer in a patient in need thereof, comprising administering to the patient an effective amount of a pharmaceutical composition comprising an antibody comprising the amino acid sequence of SEQ ID NO: 9 and the amino acid sequence of SEQ ID NO: 10, wherein said antibody specifically binds to human FGFR-3(IIIb) and FGFR-3(IIIc), and wherein said bladder cancer expresses FGFR-3(IIIb) or FGFR-3(IIIc).

2. The method of claim 1, wherein the antibody is administered together with a pharmaceutically acceptable carrier, diluent or excipient.

3. The method of claim 2, further comprising administering simultaneously, separately, or sequentially an effective amount of another agent to the patient, wherein the agent is cisplatin.

4. A method of treating bladder cancer in a patient in need thereof, comprising administering to the patient an effective amount of a pharmaceutical composition comprising an antibody comprising the amino acid sequence of SEQ ID NO: 9 and the amino acid sequence of SEQ ID NO: 10, wherein said antibody internalizes human FGFR-3, and wherein said bladder cancer comprises bladder cancer cells expressing FGFR-3(IIIb) or FGFR-3(IIIc).

5. A method of treating bladder cancer in a patient in need thereof, comprising administering to the patient an effective amount of a pharmaceutical composition comprising an antibody comprising the amino acid sequence of SEQ ID NO: 9 and the amino acid sequence of SEQ ID NO: 10, wherein said antibody depletes human FGFR-3(IIIb) or FGFR-3(IIIc) from the cell surface of bladder cancer cells in the patient.

* * * * *

SEQUENCE LISTING

```
<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: Synthetic construct

<400> SEQUENCE: 1

Gly Tyr Met Phe Thr Ser Tyr Gly Ile Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic construct

<400> SEQUENCE: 2

Trp Val Ser Thr Tyr Asn Gly Asp Thr Asn Tyr Ala Gln Lys Phe Gln
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Synthetic construct

<400> SEQUENCE: 3

Val Leu Gly Tyr Tyr Asp Ser Ile Asp Gly Tyr Tyr Tyr Gly Met Asp
1               5                   10                  15

Val

<210> SEQ ID NO 4
<211> LENGTH: 11
<212> TYPE: PRT
<213> ORGANISM: Artificial Sequence
<220> FEATURE:
<223> OTHER INFORMATION: Synthetic construct

<400> SEQUENCE: 4

Gly Gly Asn Asn Ile Gly Asp Lys Ser Val His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic construct

<400> SEQUENCE: 5

Leu Asp Thr Glu Arg Pro Ser
1               5
```

<210> SEQ ID NO 6
<211> LENGTH: 11
<212> TYPE: PRT
<213> ORGANISM: Artificial Sequence
<220> FEATURE:
<223> OTHER INFORMATION: Synthetic construct

<400> SEQUENCE: 6

Gln Val Trp Asp Ser Gly Ser Asp His Val Val
1               5                   10

<210> SEQ ID NO 7
<211> LENGTH: 126
<212> TYPE: PRT
<213> ORGANISM: Artificial Sequence
<220> FEATURE:
<223> OTHER INFORMATION: Synthetic construct

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Thr Ser Tyr
            20                  25                  30

Gly Ile Ser Trp Val Arg Gln Ala Pro Gly Gln Gly Leu Glu Trp Met
        35                  40                  45

Gly Trp Val Ser Thr Tyr Asn Gly Asp Thr Asn Tyr Ala Gln Lys Phe
    50                  55                  60

Gln Gly Arg Val Thr Val Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Val Leu Gly Tyr Tyr Asp Ser Ile Asp Gly Tyr Tyr Tyr Gly
            100                 105                 110

Met Asp Val Trp Gly Gln Gly Thr Thr Val Thr Val Ser Ser
        115                 120                 125

<210> SEQ ID NO 8
<211> LENGTH: 109
<212> TYPE: PRT
<213> ORGANISM: Artificial Sequence
<220> FEATURE:
<223> OTHER INFORMATION: Synthetic construct

<400> SEQUENCE: 8

Gln Ser Val Leu Thr Gln Pro Pro Ser Leu Ser Val Ala Pro Gly Lys
1               5                   10                  15

Thr Ala Thr Phe Thr Cys Gly Gly Asn Asn Ile Gly Asp Lys Ser Val
            20                  25                  30

His Trp Tyr Arg Gln Lys Pro Gly Gln Ala Pro Val Leu Val Met Tyr
        35                  40                  45

Leu Asp Thr Glu Arg Pro Ser Gly Ile Pro Glu Arg Met Ser Gly Ser
    50                  55                  60

Asn Phe Gly Asn Thr Ala Thr Leu Thr Ile Thr Arg Val Glu Ala Glu
65                  70                  75                  80

Asp Glu Ala Asp Tyr Tyr Cys Gln Val Trp Asp Ser Gly Ser Asp His
                85                  90                  95

Val Val Phe Gly Gly Gly Thr Lys Leu Thr Val Leu Gly
            100                 105

<210> SEQ ID NO 9

```
<211> LENGTH: 456
<212> TYPE: PRT
<213> ORGANISM: Artificial Sequence
<220> FEATURE:
<223> OTHER INFORMATION: Synthetic construct

<400> SEQUENCE: 9
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Met | Phe | Thr | Ser | Tyr |
| | | | 20 | | | | | 25 | | | | | 30 | | |
| Gly | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Trp | Val | Ser | Thr | Tyr | Asn | Gly | Asp | Thr | Asn | Tyr | Ala | Gln | Lys | Phe |
| | 50 | | | | | 55 | | | | | 60 | | | | |
| Gln | Gly | Arg | Val | Thr | Val | Thr | Thr | Asp | Thr | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Glu | Asp | Thr | Ala | Val | Tyr | Tyr | Cys |
| | | | | 85 | | | | | 90 | | | | | 95 | |
| Ala | Arg | Val | Leu | Gly | Tyr | Tyr | Asp | Ser | Ile | Asp | Gly | Tyr | Tyr | Tyr | Gly |
| | | | 100 | | | | | 105 | | | | | 110 | | |
| Met | Asp | Val | Trp | Gly | Gln | Gly | Thr | Thr | Val | Thr | Val | Ser | Ser | Ala | Ser |
| | | 115 | | | | | 120 | | | | | 125 | | | |
| Thr | Lys | Gly | Pro | Ser | Val | Phe | Pro | Leu | Ala | Pro | Ser | Ser | Lys | Ser | Thr |
| | 130 | | | | | 135 | | | | | 140 | | | | |
| Ser | Gly | Gly | Thr | Ala | Ala | Leu | Gly | Cys | Leu | Val | Lys | Asp | Tyr | Phe | Pro |
| 145 | | | | | 150 | | | | | 155 | | | | | 160 |
| Glu | Pro | Val | Thr | Val | Ser | Trp | Asn | Ser | Gly | Ala | Leu | Thr | Ser | Gly | Val |
| | | | | 165 | | | | | 170 | | | | | 175 | |
| His | Thr | Phe | Pro | Ala | Val | Leu | Gln | Ser | Ser | Gly | Leu | Tyr | Ser | Leu | Ser |
| | | | 180 | | | | | 185 | | | | | 190 | | |
| Ser | Val | Val | Thr | Val | Pro | Ser | Ser | Ser | Leu | Gly | Thr | Gln | Thr | Tyr | Ile |
| | | 195 | | | | | 200 | | | | | 205 | | | |
| Cys | Asn | Val | Asn | His | Lys | Pro | Ser | Asn | Thr | Lys | Val | Asp | Lys | Arg | Val |
| | 210 | | | | | 215 | | | | | 220 | | | | |
| Glu | Pro | Lys | Ser | Cys | Asp | Lys | Thr | His | Thr | Cys | Pro | Pro | Cys | Pro | Ala |
| 225 | | | | | 230 | | | | | 235 | | | | | 240 |
| Pro | Glu | Leu | Leu | Gly | Gly | Pro | Ser | Val | Phe | Leu | Phe | Pro | Pro | Lys | Pro |
| | | | | 245 | | | | | 250 | | | | | 255 | |
| Lys | Asp | Thr | Leu | Met | Ile | Ser | Arg | Thr | Pro | Glu | Val | Thr | Cys | Val | Val |
| | | | 260 | | | | | 265 | | | | | 270 | | |
| Val | Asp | Val | Ser | His | Glu | Asp | Pro | Glu | Val | Lys | Phe | Asn | Trp | Tyr | Val |
| | | 275 | | | | | 280 | | | | | 285 | | | |
| Asp | Gly | Val | Glu | Val | His | Asn | Ala | Lys | Thr | Lys | Pro | Arg | Glu | Glu | Gln |
| | 290 | | | | | 295 | | | | | 300 | | | | |
| Tyr | Asn | Ser | Thr | Tyr | Arg | Val | Val | Ser | Val | Leu | Thr | Val | Leu | His | Gln |
| 305 | | | | | 310 | | | | | 315 | | | | | 320 |
| Asp | Trp | Leu | Asn | Gly | Lys | Glu | Tyr | Lys | Cys | Lys | Val | Ser | Asn | Lys | Ala |
| | | | | 325 | | | | | 330 | | | | | 335 | |
| Leu | Pro | Ala | Pro | Ile | Glu | Lys | Thr | Ile | Ser | Lys | Ala | Lys | Gly | Gln | Pro |
| | | | 340 | | | | | 345 | | | | | 350 | | |
| Arg | Glu | Pro | Gln | Val | Tyr | Thr | Leu | Pro | Pro | Ser | Arg | Glu | Glu | Met | Thr |
| | | 355 | | | | | 360 | | | | | 365 | | | |
| Lys | Asn | Gln | Val | Ser | Leu | Thr | Cys | Leu | Val | Lys | Gly | Phe | Tyr | Pro | Ser |
| | 370 | | | | | 375 | | | | | 380 | | | | |

```
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
        450                 455

<210> SEQ ID NO 10
<211> LENGTH: 214
<212> TYPE: PRT
<213> ORGANISM: Artificial Sequence
<220> FEATURE:
<223> OTHER INFORMATION: Synthetic construct

<400> SEQUENCE: 10

Gln Ser Val Leu Thr Gln Pro Pro Ser Leu Ser Val Ala Pro Gly Lys
1               5                   10                  15

Thr Ala Thr Phe Thr Cys Gly Gly Asn Asn Ile Gly Asp Lys Ser Val
            20                  25                  30

His Trp Tyr Arg Gln Lys Pro Gly Gln Ala Pro Val Leu Val Met Tyr
        35                  40                  45

Leu Asp Thr Glu Arg Pro Ser Gly Ile Pro Glu Arg Met Ser Gly Ser
    50                  55                  60

Asn Phe Gly Asn Thr Ala Thr Leu Thr Ile Thr Arg Val Glu Ala Glu
65                  70                  75                  80

Asp Glu Ala Asp Tyr Tyr Cys Gln Val Trp Asp Ser Gly Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Ala Glu Cys Ser
    210

<210> SEQ ID NO 11
<211> LENGTH: 795
<212> TYPE: PRT
<213> ORGANISM: Homo sapiens

<400> SEQUENCE: 11

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30
```

```
Gly Arg Ala Ala Glu Val Pro Gly Pro Glu Pro Gly Gln Glu Leu Val
            35                  40                  45

Phe Gly Ser Gly Asp Ala Val Glu Leu Ser Cys Pro Pro Gly Gly
     50                  55                  60

Gly Pro Met Gly Pro Thr Val Trp Val Lys Asp Gly Thr Gly Leu Val
 65                  70                  75                  80

Pro Ser Glu Arg Val Leu Val Gly Pro Gln Arg Leu Val Leu Asn Ala
                 85                  90                  95

Ser His Glu Asp Ser Gly Ala Tyr Ser Cys Arg Gln Arg Leu Thr Arg
                100                 105                 110

Val Leu Cys His Phe Ser Val Arg Val Thr Asp Ala Pro Ser Ser Gly
             115                 120                 125

Asp Asp Glu Asp Gly Glu Asp Glu Ala Glu Asp Thr Gly Val Asp Thr
         130                 135                 140

Gly Ala Pro Tyr Trp Thr Arg Pro Glu Arg Met Asp Lys Lys Leu Leu
145                 150                 155                 160

Ala Val Pro Ala Ala Asn Thr Val Arg Phe Arg Cys Pro Ala Ala Gly
                165                 170                 175

Asn Pro Thr Pro Ser Ile Ser Trp Leu Lys Asn Gly Arg Glu Phe Arg
             180                 185                 190

Gly Glu His Arg Ile Gly Gly Ile Lys Leu Arg His Gln Gln Trp Ser
         195                 200                 205

Leu Val Met Glu Ser Val Val Pro Ser Asp Arg Gly Asn Tyr Thr Cys
     210                 215                 220

Val Val Glu Asn Lys Phe Gly Ser Ile Arg Gln Thr Tyr Thr Leu Asp
225                 230                 235                 240

Val Leu Glu Arg Ser Pro His Arg Pro Ile Leu Gln Ala Gly Leu Pro
                245                 250                 255

Ala Asn Gln Thr Ala Val Leu Gly Ser Asp Val Glu Phe His Cys Lys
             260                 265                 270

Val Tyr Ser Asp Ala Pro His Ile Gln Trp Leu Lys His Val Glu Val
         275                 280                 285

Asn Gly Ser Lys Val Gly Pro Asp Gly Thr Pro Tyr Val Thr Val Leu
     290                 295                 300

Lys Thr Ala Gly Ala Asn Thr Thr Asp Lys Glu Leu Glu Val Leu Ser
305                 310                 315                 320

Leu His Asn Val Thr Phe Glu Asp Ala Gly Glu Tyr Thr Cys Leu Ala
                325                 330                 335

Gly Asn Ser Ile Gly Phe Ser His His Ser Ala Trp Leu Val Val Leu
             340                 345                 350

Pro Ala Glu Glu Glu Leu Val Glu Ala Asp Glu Ala Gly Ser Val Tyr
         355                 360                 365

Ala Gly Ile Leu Ser Tyr Gly Val Gly Phe Phe Leu Phe Ile Leu Val
     370                 375                 380

Val Ala Ala Val Thr Leu Cys Arg Leu Arg Ser Pro Lys Lys Gly
385                 390                 395                 400

Leu Gly Ser Pro Thr Val His Lys Ile Ser Arg Phe Pro Leu Lys Arg
                405                 410                 415

Gln Val Ser Leu Glu Ser Asn Ala Ser Asn Ser Ser Asn Thr Pro Leu
             420                 425                 430

Val Arg Ile Ala Arg Leu Ser Ser Gly Glu Gly Pro Thr Leu Ala Asn
         435                 440                 445

Val Ser Glu Leu Glu Leu Pro Ala Asp Pro Lys Trp Glu Leu Ser Arg
```

```
            450                 455                 460
Ala Arg Leu Thr Leu Gly Lys Pro Leu Gly Glu Gly Cys Phe Gly Gln
465                 470                 475                 480

Val Val Met Ala Glu Ala Ile Gly Ile Asp Lys Asp Arg Ala Ala Lys
                485                 490                 495

Pro Val Thr Val Ala Val Lys Met Leu Lys Asp Asp Ala Thr Asp Lys
                500                 505                 510

Asp Leu Ser Asp Leu Val Ser Glu Met Glu Met Met Lys Met Ile Gly
                515                 520                 525

Lys His Lys Asn Ile Ile Asn Leu Leu Gly Ala Cys Thr Gln Gly Gly
                530                 535                 540

Pro Leu Tyr Val Leu Val Glu Tyr Ala Ala Lys Gly Asn Leu Arg Glu
545                 550                 555                 560

Phe Leu Arg Ala Arg Arg Pro Pro Gly Leu Asp Tyr Ser Phe Asp Thr
                565                 570                 575

Cys Lys Pro Pro Glu Glu Gln Leu Thr Phe Lys Asp Leu Val Ser Cys
                580                 585                 590

Ala Tyr Gln Val Ala Arg Gly Met Glu Tyr Leu Ala Ser Lys Cys Ile
                595                 600                 605

His Arg Asp Leu Ala Ala Arg Asn Val Leu Val Thr Glu Asp Asn Val
610                 615                 620

Met Lys Ile Ala Asp Phe Gly Leu Ala Arg Asp Val His Asn Leu Asp
625                 630                 635                 640

Tyr Tyr Lys Lys Thr Thr Asn Gly Arg Leu Pro Val Lys Trp Met Ala
                645                 650                 655

Pro Glu Ala Leu Phe Asp Arg Val Tyr Thr His Ser Asp Val Ser Phe
                660                 665                 670

Gly Val Leu Leu Trp Glu Ile Phe Thr Leu Gly Gly Ser Pro Tyr Pro
                675                 680                 685

Gly Ile Pro Val Glu Glu Leu Phe Lys Leu Leu Lys Glu Gly His Arg
                690                 695                 700

Met Asp Lys Pro Ala Asn Cys Thr His Asp Leu Tyr Met Ile Met Arg
705                 710                 715                 720

Glu Cys Trp His Ala Ala Pro Ser Arg Pro Thr Phe Lys Leu Val Glu
                725                 730                 735

Asp Leu Asp Arg Val Leu Thr Val Thr Ser Thr Asp Glu Tyr Leu Asp
                740                 745                 750

Leu Ser Ala Pro Phe Glu Tyr Ser Pro Gly Gly Gln Asp Thr Pro Ser
                755                 760                 765

Ser Ser Ser Ser Gly Asp Asp Ser Val Phe Ala His Asp Leu Leu Pro
770                 775                 780

Pro Ala Pro Pro Ser Ser Gly Gly Ser Arg Thr
785                 790                 795

<210> SEQ ID NO 12
<211> LENGTH: 100
<212> TYPE: PRT
<213> ORGANISM: Homo sapiens

<400> SEQUENCE: 12

Ala Pro Tyr Trp Thr Arg Pro Glu Arg Met Asp Lys Lys Leu Leu Ala
1               5                   10                  15

Val Pro Ala Ala Asn Thr Val Arg Phe Arg Cys Pro Ala Ala Gly Asn
                20                  25                  30

Pro Thr Pro Ser Ile Ser Trp Leu Lys Asn Gly Arg Glu Phe Arg Gly
```

```
                35                      40                      45
Glu His Arg Ile Gly Gly Ile Lys Leu Arg His Gln Gln Trp Ser Leu
    50                  55                  60

Val Met Glu Ser Val Val Pro Ser Asp Arg Gly Asn Tyr Thr Cys Val
65                  70                  75                  80

Val Glu Asn Lys Phe Gly Ser Ile Arg Gln Thr Tyr Thr Leu Asp Val
                85                  90                  95

Leu Glu Arg Ser
            100
```